United States Patent
Li et al.

(10) Patent No.: US 9,597,164 B2
(45) Date of Patent: Mar. 21, 2017

(54) TACTILE OBJECTS FOR ORTHODONTICS, SYSTEMS AND METHODS

(71) Applicant: Align Technology, Inc., San Jose, CA (US)

(72) Inventors: Chunhua Li, Cupertino, CA (US); Jennifer Chen, San Francisco, CA (US); John Morton, San Jose, CA (US); Jon Moss, Antioch, CA (US); Clark Kaufhardt, Danville, CA (US); Heng Cao, Santa Clara, CA (US)

(73) Assignee: Align Technology, Inc., San Jose, CA (US)

( * ) Notice: Subject to any disclaimer, the term of this patent is extended or adjusted under 35 U.S.C. 154(b) by 244 days.

(21) Appl. No.: 14/206,836

(22) Filed: Mar. 12, 2014

(65) Prior Publication Data

US 2014/0193767 A1 Jul. 10, 2014

Related U.S. Application Data

(62) Division of application No. 12/633,715, filed on Dec. 8, 2009, now Pat. No. 8,708,697.

(51) Int. Cl.
*A61C 7/08* (2006.01)

(52) U.S. Cl.
CPC ........... *A61C 7/08* (2013.01); *Y10T 29/49568* (2015.01)

(58) Field of Classification Search
CPC .................................................... A61C 7/08
See application file for complete search history.

(56) References Cited

U.S. PATENT DOCUMENTS

| | | |
|---|---|---|
| 2,467,432 A | 4/1949 | Kesling |
| 3,407,500 A | 10/1968 | Kesling |
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |

(Continued)

FOREIGN PATENT DOCUMENTS

| | | |
|---|---|---|
| AU | 3031677 A | 5/1979 |
| AU | 517102 B2 | 7/1981 |

(Continued)

OTHER PUBLICATIONS

AADR. American Association for Dental Research, Summary of Activities, Mar. 20-23, 1980, Los Angeles, CA, p. 195.

(Continued)

*Primary Examiner* — Edward Moran
(74) *Attorney, Agent, or Firm* — Wilson Sonsini Goodrich & Rosati

(57) ABSTRACT

Methods, systems, and apparatus's for improving orthodontic treatments. In an embodiment, an orthodontic system including a tactile object is provided for modulating an engagement between a tooth attachment and an orthodontic appliance.

18 Claims, 18 Drawing Sheets

(56) References Cited

U.S. PATENT DOCUMENTS

| | | |
|---|---|---|
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,482,298 B1 | 11/2002 | Bhatnagar |
| 6,485,298 B2 | 11/2002 | Chishti et al. |
| 6,524,101 B1 | 2/2003 | Phan et al. |
| 6,554,611 B2 | 4/2003 | Chishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 6,830,450 B2 | 12/2004 | Knopp et al. |
| 7,059,850 B1 | 6/2006 | Phan et al. |
| 8,708,697 B2 | 4/2014 | Li et al. |
| 2002/0006597 A1 | 1/2002 | Andreiko et al. |
| 2003/0009252 A1 | 1/2003 | Pavlovskaia et al. |
| 2003/0139834 A1 | 7/2003 | Nikolskiy et al. |
| 2003/0224311 A1 | 12/2003 | Cronauer |
| 2004/0128010 A1 | 7/2004 | Pavlovskaia et al. |
| 2005/0055118 A1 | 3/2005 | Nikolskiy et al. |
| 2006/0093983 A1 | 5/2006 | Schultz |
| 2007/0065768 A1* | 3/2007 | Nadav .................. A61C 7/006 433/6 |

(56) References Cited

U.S. PATENT DOCUMENTS

| | | | |
|---|---|---|---|
| 2008/0233529 | A1 | 9/2008 | Kuo et al. |
| 2011/0136072 | A1 | 6/2011 | Li et al. |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |

OTHER PUBLICATIONS

Alcaniz, et al, "An Advanced System for the Simulation and Planning of Orthodontic Treatments," Karl HF Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.
Alexander et al., "The DigiGraph Work Station Part 2 Clinical Management," JCO, pp. 402-407 (Jul. 1990).
Altschuler et al., "Analysis of 3-D Data for Comparative 3-D Serial Growth Pattern Studies of Oral-Facial Structures, " AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.
Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space-Coded by a Laser-Projected Dot Matrix," SPIE Imaging Applications for Automated Industrial Inspection and Assembly, vol. 182, p. 187-191 (1979).
Altschuler, "3D Mapping of Maxillo-Facial Prosthesis," AADR Abstract #607, 2 pages total, (1980).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of III., Aug. 26-30, 1975, pp. 142-166.
Baumrind, "Integrated Three-Dimensional Craniofacial Mapping: Background, Principles, and Perspectives," Semin in Orthod., 7(4):223-232 (Dec. 2001).
Begole et al., "A Computer System for the Analysis of Dental Casts," The Angle Orthod., 51(3):253-259 (Jul. 1981).
Bernard et al., "Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff et al., "Computerized Analysis of Occlusion in the Postcanine Dentition," Am. J. Orthod., 61(3): 245-254 (Mar. 1972).
Biggerstaff, "Computerized Diagnostic Setups and Simulations," Angle Orthod., 40(1):28-36 (Jan. 1970).
Biostar Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL <http://astronomy.swin.edu.au/pbourke/prolection/coords>.
Boyd et al., "Three Dimensional Diagnosis and Orthodontic Treatment of Complex Malocclusions With the Invisalign Appliance," Semin Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: IK Comparison with Manual Measurements of Mesio-distal Diameter," J. Dent. Res., 65(3):428-431 (Mar. 1986).
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Burstone et al., Precision Adjustment of the Transpalatal Lingual Arch: Computer Arch Form in Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.

(56) References Cited

OTHER PUBLICATIONS

Curry et al., "Integrated Three-Dimensional Craniofacial Mapping at the Craniofacial Research Instrumentation Laboratory/University of the Pacific," Semin Orthod., 7(4):258-265 (Dec. 2001).

Cutting et al., "Three-Dimensional Computer-Assisted Design of Craniofacial Surgical Procedures: Optimization and Interaction with Cephalometric and CT-Based Models," Plast. 77(6):877-885 (Jun. 1986).

DCS Dental AG, "The CAD/CAM 'DCS Titan System' for Production of Crowns/Bridges," DSC Production AG, pp. 1-7 (Jan. 1992).

Definition for gingiva. Dictionary.com p. 1-3. Retrieved from the internet Nov. 5, 2004 <http://reference.com/search/search?q=gingiva>.

DeFranco et al., "Three-Dimensional Large Displacement Analysis of Orthodontic Appliances," J. Biomechanics, 9:793-801 (1976).

Dental Institute University of Zurich Switzerland, Program for International Symposium JD on Computer Restorations: State of the Art of the CEREC-Method, May 1991, 2 pages total.

Dentrac Corporation, Dentrac document, pp. 4-13 (1992).

DENT-X posted on Sep. 24, 1998 at <http://www.dent-x.com/DentSim.htm>, 6 pages.

Doyle, "Digital Dentistry," Computer Graphics World, pp. 50-52, 54 (Oct. 2000).

DuraClearTM product information, Allesee Orthodontic Appliances-Pro Lab, 1 page (1997).

Duret et al, "CAD-CAM in Dentistry," J. Am. Dent. Assoc. 117:715-720 (Nov. 1988).

Duret et al., "CAD/CAM Imaging in Dentistry," Curr. Opin. Dent., 1:150-154 (1991).

Duret, "The Dental CAD/CAM, General Description of the Project," Hennson International Product Brochure, 18 pages total, Jan. 1986.

Duret,"Vers Une Prosthese Informatisee," (English translation attached), Tonus, vol. 75, pp. 55-57 (Nov. 15, 1985).

Economides, "The Microcomputer in the Orthodontic Office," JCO, pp. 767-772 (Nov. 1979).

Elsasser, Some Observations on the History and Uses of the Kesling Positioner, Am. J. Orthod. (1950) 36:368-374.

English translation of Japanese Laid-Open Publication No. 63-11148 to inventor T. Ozukuri (Laid-Open on Jan. 18, 1998) pp. 1-7.

Felton et al., "A Computerized Analysis of the Shape and Stability of Mandibular Arch Form," Am. J. Orthod. Dentofacial Orthop., 92(6):478-483 (Dec. 1987).

Friede et al., "Accuracy of Cephalometric Prediction in Orthognathic Surgery," Abstract of Papers, J. Dent. Res., 70:754-760 (1987).

Futterling et a/., "Automated Finite Element Modeling of a Human Mandible with Dental Implants," JS WSCG '98—Conference Program, retrieved from the Internet: <http://wscg.zcu.cz/wscg98/papers98/Strasser 98.pdf>, 8 pages.

Gao et al., "3-D element Generation for Multi-Connected Complex Dental and Mandibular Structure," Proc. Intl Workshop on Medical Imaging and Augmented Reality, pp. 267-271 (Jun. 12, 2001).

Gim-Alldent Deutschland, "Das DUX System: Die Technik," 2 pages total (2002).

Gottleib et al., "JCO Interviews Dr. James A. McNamara, Jr., on the Frankel Appliance: Part 2: Clinical 1-1 Management, "J. Clin. Orthod., 16(6):390-407 (Jun. 1982).

Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).

Guess et al., "Computer Treatment Estimates in Orthodontics and Orthognathic Surgery," JCO, pp. 262-28 (Apr. 1989).

Heaven et al. "Computer-Based Image Analysis of Artificial Root Surface Caries," Abstracts of Papers, J. Dent. Res., 70:528 (Apr. 17-21, 1991).

Highbeam Research, "Simulating Stress Put on Jaw," Tooling & Production [online], Nov. 1996, n pp. 1-2, retrieved from the Internet on Nov. 5, 2004, URL http://static .highbeam.com/t/toolingampproduction/november011996/simulatingstressputonfa . . .>.

Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).

Hoffmann, et al., "Role of Cephalometry for Planning of Jaw Orthopedics and Jaw Surgery Procedures," 0 (Article Summary in English, article in German), lnformatbnen, pp. 375-396 (Mar. 1991).

Hojjatie et al., "Three-Dimensional Finite Element Analysis of Glass-Ceramic Dental Crowns," J. Biomech., 23(11):1157-1166 (1990).

Huckins, "CAD-CAM Generated Mandibular Model Prototype from MRI Data," AAOMS, p. 96 (1999).

Important Tip About Wearing the Red White & Blue Active Clear Retainer System, Allesee Orthodontic Appliances-Pro Lab, 1 page 1998).

Inside the ADA, JADA, 118:286-294 (Mar. 1989).

JCO Interviews, Craig Andreiko , DDS, MS on the Elan and Orthos Systems, JCO, pp. 459-468 (Aug. 1994).

JCO Interviews, Dr. Homer W. Phillips on Computers in Orthodontic Practice, Part 2, JCO. 1997; 1983:819-831.

Jerrold, "The Problem, Electronic Data Transmission and the Law," AJO-DO, pp. 478-479 (Apr. 1988).

Jones et al., "An Assessment of the Fit of a Parabolic Curve to Pre- and Post-Treatment Dental Arches," Br. J. Orthod., 16:85-93 (1989).

JP Faber et al., "Computerized Interactive Orthodontic Treatment Planning," Am. J. Orthod., 73(1):36-46. Jan. 1978.

Kamada et.al., Construction of Tooth Positioners with LTV Vinyl Silicone Rubber and Some Case KJ Reports, J. Nihon University School of Dentistry (1982) 24(1):1-27.

Kanazawa et al., "Three-Dimensional Measurements of the Occlusal Surfaces of Upper Molars in a Dutch Population," J. Dent Res., 63(11):1298-1301 (Nov. 1984).

Kesling et al., The Philosophy of the Tooth Positioning Appliance, American Journal of Orthodontics and Oral surgery. 1945; 31:297-304.

Kesling, Coordinating the Predetermined Pattern and Tooth Positioner with Conventional Treatment, KN Am. J. Orthod. Oral Surg. (1946) 32:285-293.

Ki Kamada et.al., Case Reports on Tooth Positioners Using LTV Vinyl Silicone Rubber, J. Nihon University School of Dentistry (1984) 26(1): 11-29.

Kleeman et al., The Speed Positioner, J. Clin. Orthod. (1996) 30:673-680.

Kochanek, "Interpolating Splines with Local Tension, Continuity and Bias Control," Computer Graphics, ri 18(3):33-41 (Jul. 1984).

KM Oral Surgery (1945) 31 :297-30.

Kunii et al., "Articulation Simulation for an Intelligent Dental Care System," Displays 15:181-188 (1994).

Kuroda et al., Three-Dimensional Dental Cast Analyzing System Using Laser Scanning, Am. J. Orthod. Dentofac. Orthop. (1996) 110:365-369.

Laminated. (n.d.). Dictionary.com Unabridged. Retrieved Apr. 28, 2010, from Dictionary.com website: http://dictionary.reference.com/browse/Laminated.

Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).

Leinfelder, et al., "A New Method for Generating Ceramic Restorations: a CAD-CAM System," J. Am. 1-1 Dent. Assoc., 118(6):703-707 (Jun. 1989).

Manetti, et al., "Computer-Aided Cefalometry and New Mechanics in Orthodontics," (Article Summary in English, article in German), Fortschr Kieferorthop. 44, 370-376 (Nr. 5), 1983.

McCann, "Inside the ADA," J. Amer. Dent. Assoc., 118:286-294 (Mar. 1989).

(56) References Cited

OTHER PUBLICATIONS

McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy as One, Two, Three," AOA/Pro Corner, vol. 11, No. 1, 2 pages (2002).
Mormann et al., "Marginale Adaptation von adhasuven Porzellaninlays in vitro," Separatdruck aus:Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993—Abstract Collection," 28: 3-7.
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and q Essix Appliances, <http//www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et a/., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," LM Annual International Conference of the IEEE Engineering in Medicine and Biology Society, 13(1):344-345 1991.
Rekow, "A Review of the Developments in Dental CAD/CAM Systems," (contains references to LN Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210, 309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice is Clear: Red, White & Blue . . . The Simple, Affordable, No-Braces Treatment, Allesee HI Orthodontic Appliances-Pro Lab product information for doctors. http://ormco.com/aoa/appliances-services/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients, <http://ormco.com/aoa/appliancesservices/RWB/patients.html>, 2 pages (May 19, 2003).
The Choice is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.

(56) References Cited

OTHER PUBLICATIONS

Williams, "Dentistry and CAD/CAM: Another French Revolution," J. Dent. Practice Admin., pp. 2-5 (Jan./Mar. 1987).

Williams, "The Switzerland and Minnesota Developments in CAD/CAM," J. Dent. Practice Admin., pp. 50-55 (Apr./Jun. 1987).

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); Ill.—The General Concept of the D.P. Method and Its Therapeutic Effect, Part 2. Skeletal Reversed Occlusion Case Reports," Nippon Dental Review, 458:112-129 (Dec. 1980).

Yoshii, "Research on a New Orthodontic Appliance: The Dynamic Positioner (D.P.); Ill. The General Concept of the D.P. Method and Its Therapeutic Effect, Part 1, Dental and Functional Reversed Occlusion Case Reports," Nippon Dental Review, 457:146-164 (Nov. 1980).

You May Be a Candidate for This Invisible No-Braces Treatment, Allesee Orthodontic Appliances-Pro Lab product information for patients, 2 pages (2002).

\* cited by examiner

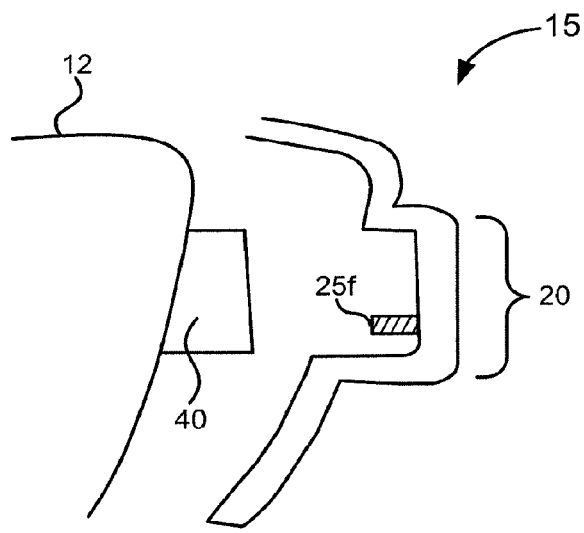 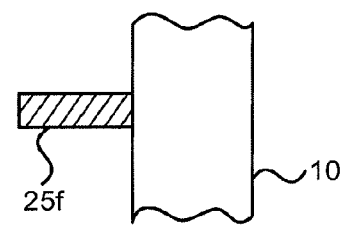
FIG. 5A  FIG. 5B
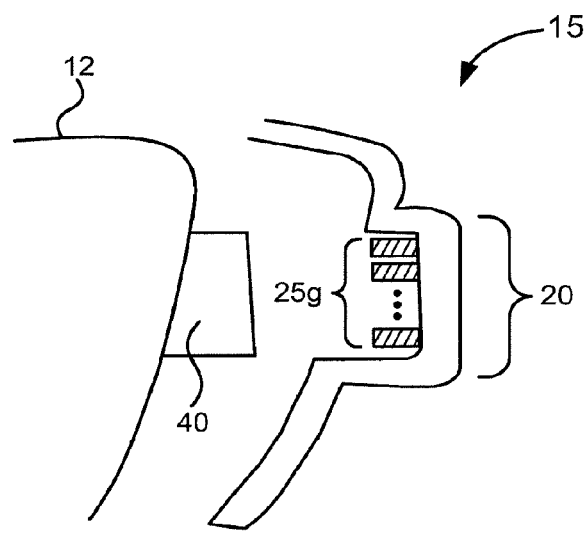 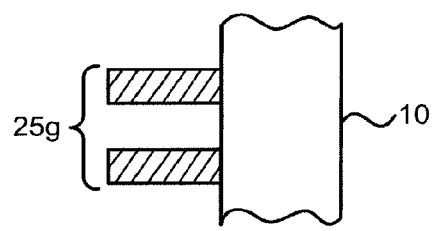
FIG. 5C  FIG. 5D

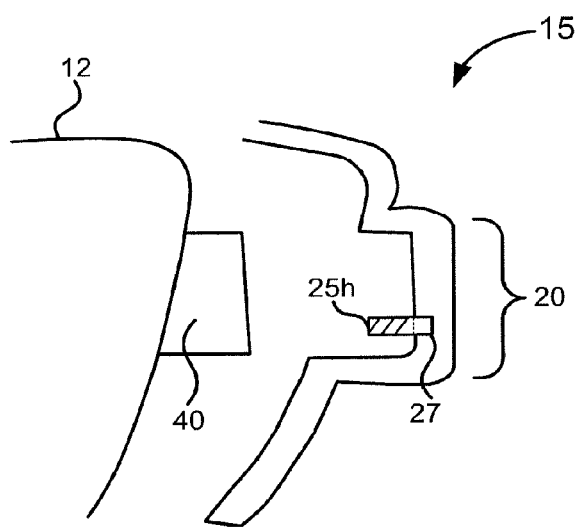
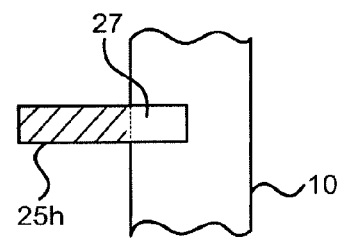
FIG. 5E  FIG. 5F
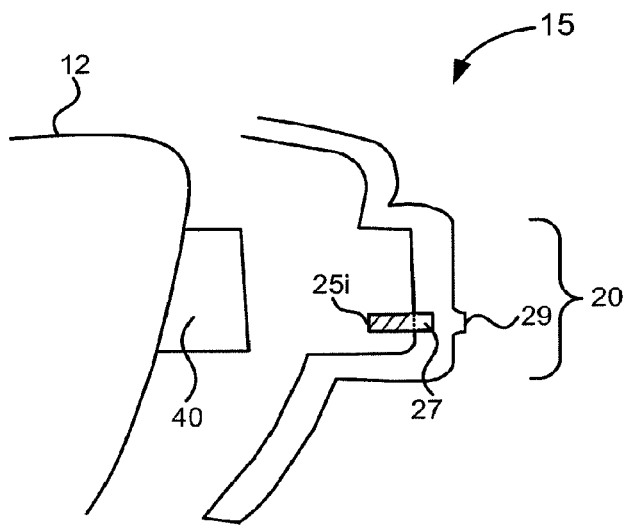
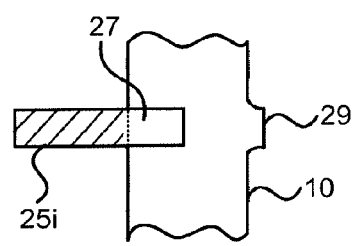
FIG. 5G  FIG. 5H

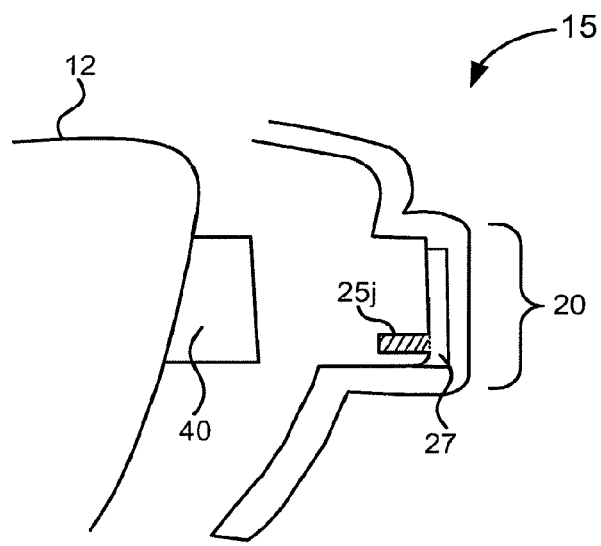
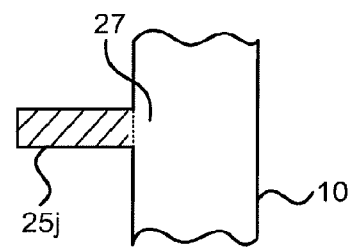
FIG. 5I  FIG. 5J
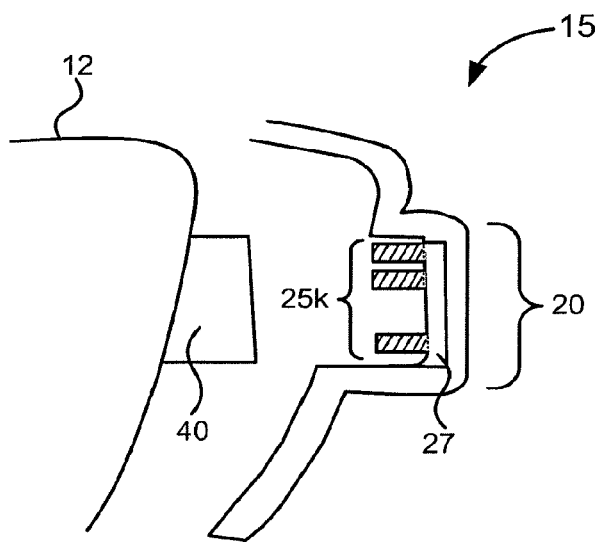
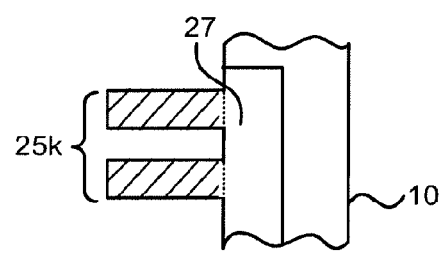
FIG. 5K  FIG. 5L

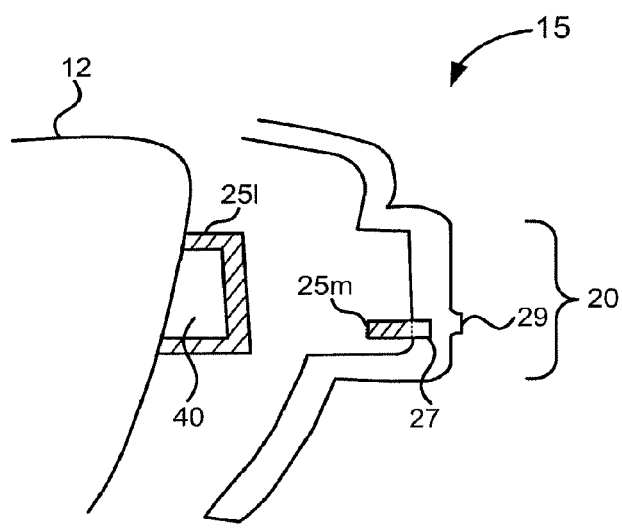
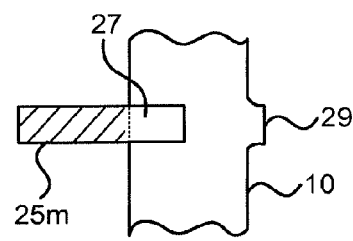
FIG. 5M
FIG. 5N
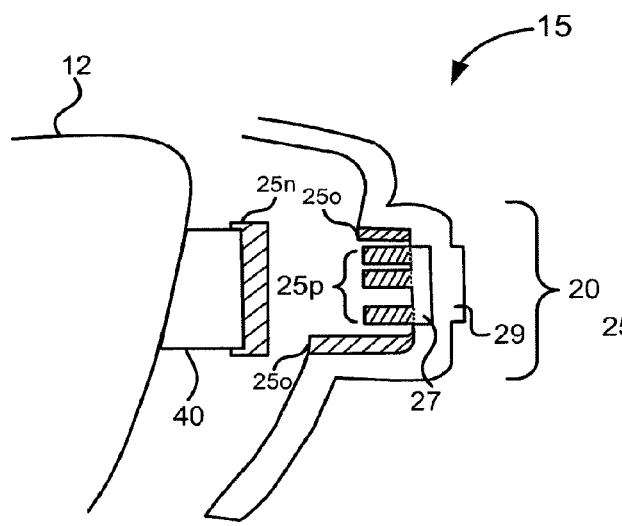
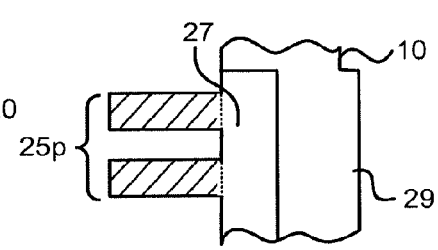
FIG. 5O
FIG. 5P

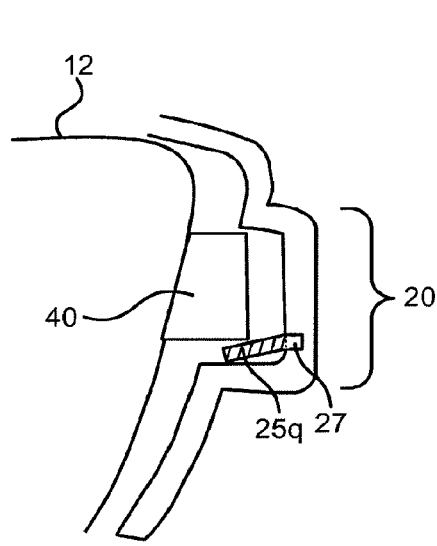
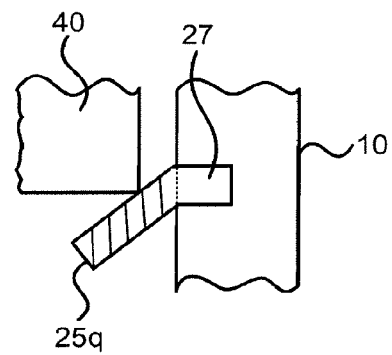
FIG. 5Q                              FIG. 5R
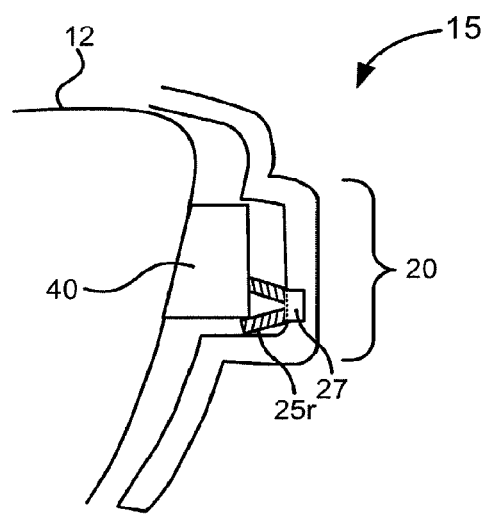
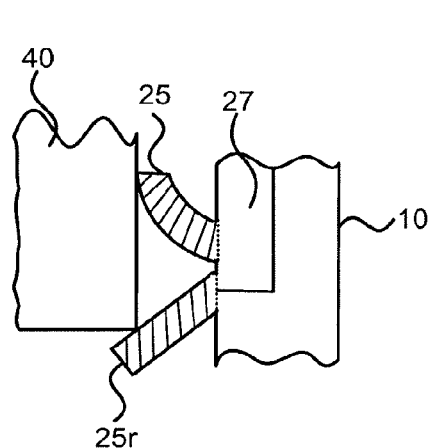
FIG. 5S                              FIG. 5T

TACTILE OBJECTS FOR ORTHODONTICS, SYSTEMS AND METHODS

CROSS-REFERENCE

This application is a divisional of U.S. application Ser. No. 12/633,715, filed Dec. 8, 2009, now U.S. Pat. No. 8,708,697, issued Apr. 29, 2014, the contents of which is hereby incorporated by reference in its entirety.

BACKGROUND OF THE INVENTION

The present invention relates generally to the field of orthodontics, and more particularly to orthodontic appliances, such as shell appliances, and tactile objects for improving the affects of attachment devices.

An objective of orthodontics is to move a patient's teeth to positions where function and/or aesthetics are optimized. Traditionally, appliances such as braces are applied to the patient's teeth by an orthodontist or dentist and the set of braces exerts continual force on the teeth and gradually urges them toward their intended positions. Over time and with a series of clinical visits, the orthodontist adjusts the appliances to move the teeth toward their final destination.

More recently, alternatives to conventional orthodontic treatment with traditional affixed appliances (e.g., braces) have become available. For example, systems including a series of preformed orthodontic appliances have become commercially available from Align Technology, Inc., Santa Clara, Calif., under the trade name Invisalign® System. An Invisalign® System appliance can be made from thin clear plastic and have teeth receiving cavities. In use, the appliance is placed over the patient's teeth and is removable. Shell-shaped orthodontic appliances are designed to impart positioning or repositioning forces to the patient's teeth. The imparted forces are resilient in nature and are associated with corresponding appliance elastic deformation. When used to reposition teeth, a series of individual appliances are worn by a patient to elastically reposition the patient's teeth over time. When used to retain teeth, one or more identical appliances are worn to restrain a patient's teeth in their current arrangement.

Attachment devices coupled to teeth have been utilized in orthodontic treatment and can improve force delivery and/or repositioning of the teeth, e.g., with shell-shaped appliances. Attachments can include those fabricated prior to tooth attachment or may be substantially assembled at the orthodontic practitioner's office prior to or in conjunction with positioning on the patient's tooth (e.g., molded composites, etc.). Use of attachment devices in conjunction with shell-type appliances may be desired for anchoring an appliance to the patient's dentition, eliciting a tooth movement, including eliciting certain movements or more difficult movements, such as more difficult rotation or intrusion/extrusion type movements.

In some instances where tooth attachments are utilized, actual force application to the patient's teeth may differ from the desired or intended force. Errors may occur as attachments made by the practitioner may not always conform to a prescribed or ideally desired shape and/or may not bond in the correct location or orientation. Manufacturing limits or errors in attachment or appliance formation (e.g., attachment receiving well of an appliance) may lead to error in appliance/attachment engagement, such as misalignment or less than ideal coupling between an attachment and appliance. Additionally, wear on an attachment and/or appliance, shape degradation of an appliance, and the like during orthodontic treatment and/or repeated insertion and removal of an appliance may occur, which can further effect force application to the patient's teeth. Accordingly, a corresponding orthodontic appliance may not ideally couple with the attachment as intended, leading to errors in force delivery and the patient's orthodontic treatment.

Accordingly, improved methods, systems, and apparatus's are needed for more optimal or precise tooth movement force delivery in orthodontic treatments utilizing tooth attachments.

BRIEF SUMMARY OF THE INVENTION

The present invention provides improved methods, systems, and apparatus's for orthodontic treatment and positioning of a patient's teeth utilizing an orthodontic appliance (e.g., patient removable shell appliance) and a tooth attachment for engaging the orthodontic appliance.

In one aspect an orthodontic positioning appliance is provided. The orthodontic positioning appliance includes a patient removable orthodontic tooth positioning appliance having teeth receiving cavities, where at least one of the teeth receiving cavities includes an attachment receiving well for engaging an attachment. The orthodontic positioning appliance further includes a tactile object disposed proximate to the attachment receiving well.

In another aspect, a method for applying a tooth positioning force to the dentition of a patient is provided. The method includes providing a patient removable orthodontic tooth positioning appliance having teeth receiving cavities and an attachment receiving well. The method further includes providing an attachment on at least one of the patient's teeth, and providing a tactile object for disposal between the attachment receiving well and the attachment. Methods and systems for generating or manufacturing an orthodontic appliance and/or orthodontic positioning system utilizing tooth attachments are also provided herein.

For a fuller understanding of the nature and advantages of the present invention, reference should be made to the ensuing detailed description and accompanying drawings. Other aspects, objects and advantages of the invention will be apparent from the drawings and detailed description that follows.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5A illustrates an attachment device, appliance, and tactile object according to a sixth embodiment.

FIG. 5B illustrates a magnified portion of FIG. 5A.

FIG. 5C illustrates an attachment device, appliance, and tactile object according to a seventh embodiment.

FIG. 5D illustrates a magnified portion of FIG. 5C.

FIG. 5E illustrates an attachment device, appliance, and tactile object according to a eighth embodiment.

FIG. 5F illustrates a magnified portion of FIG. 5E.

FIG. 5G illustrates an attachment device, appliance, and tactile object according to a ninth embodiment.

FIG. 5H illustrates a magnified portion of FIG. 5G.

FIG. 5I illustrates an attachment device, appliance, and tactile object according to a tenth embodiment.

FIG. 5J illustrates a magnified portion of FIG. 5I.

FIG. 5K illustrates an attachment device, appliance, and tactile object according to a eleventh embodiment.

FIG. 5L illustrates a magnified portion of FIG. 5K.

FIG. 5M illustrates an attachment device, appliance, and tactile object according to a twelfth embodiment.

FIG. 5N illustrates a magnified portion of FIG. 5M.

FIG. 5O illustrates an attachment device, appliance, and tactile object according to a thirteenth embodiment.

FIG. 5P illustrates a magnified portion of FIG. 5O.

FIG. 5Q illustrates an attachment device, appliance, and tactile object according to a fourteenth embodiment.

FIG. 5R illustrates a magnified portion of FIG. 5Q.

FIG. 5S illustrates an attachment device, appliance, and tactile object according to a fifteenth embodiment.

FIG. 5T illustrates a magnified portion of FIG. 5S.

DETAILED DESCRIPTION OF THE INVENTION

The present invention provides improved methods, systems, and apparatus's for orthodontic treatment and positioning of a patient's teeth utilizing an orthodontic appliance (e.g., patient removable shell appliance) engaging a tooth attachment. According to the present invention, a tactile object is disposed between an orthodontic appliance and an attachment device so as to modulate engagement between the attachment and appliance and/or force delivery as the appliance is worn by the patient. The present invention may advantageously result in any or all of the following: an increase in the quality of a fit of the attachment to the orthodontic appliance; an increase in or selection of a treatment affect (e.g., tooth movement force delivery); a reduction in degradation of an attachment over time; an increase in the predictability of forces generated by an orthodontic appliance and thus the predictability of a patient's treatment; a reduction in a patient's treatment time; an increase in an effectiveness of an orthodontic appliance; and a reduction in a cost of a patient's orthodontic treatment.

The term "tactile object" as used herein generally refers to a component or plurality of components in an orthodontic treatment system that affects an engagement between an orthodontic appliance and a corresponding attachment device disposed on a patient's tooth. Engagement may be affected by modulating a fit between an attachment and an appliance and/or affecting a tooth movement or positioning force applied to the patient's dentition as the appliance is worn by the patient. An attachment based orthodontic treatment delivery system will typically include an attachment that can be bonded to or otherwise coupled to a patient's tooth and an orthodontic appliance that couples with the attachment on the tooth when the appliance is worn by the patient or utilized for tooth position force application to the patient's dentition. A tactile object of the present invention can be disposed or positioned relative to the attachment and attachment engaging portion (e.g., attachment receiving well) of the orthodontic appliance so as to affect engagement between the attachment and the orthodontic appliance. For example, a tactile object can be disposed at least partially between the attachment and attachment receiving well of the appliance. As further described below, a tactile object may, e.g., be disposed at least partially in an attachment receiving well, proximate to an attachment receiving well, and/or disposed over or coupled to one or more surfaces of the attachment or the orthodontic appliance. A tactile object can, in some instances, include the attachment itself or a portion thereof, e.g., where the attachment is shaped or designed to affect attachment/appliance engagement. In some instances, a tactile object may be removable and/or disposable following coupling or use.

Figure 1:
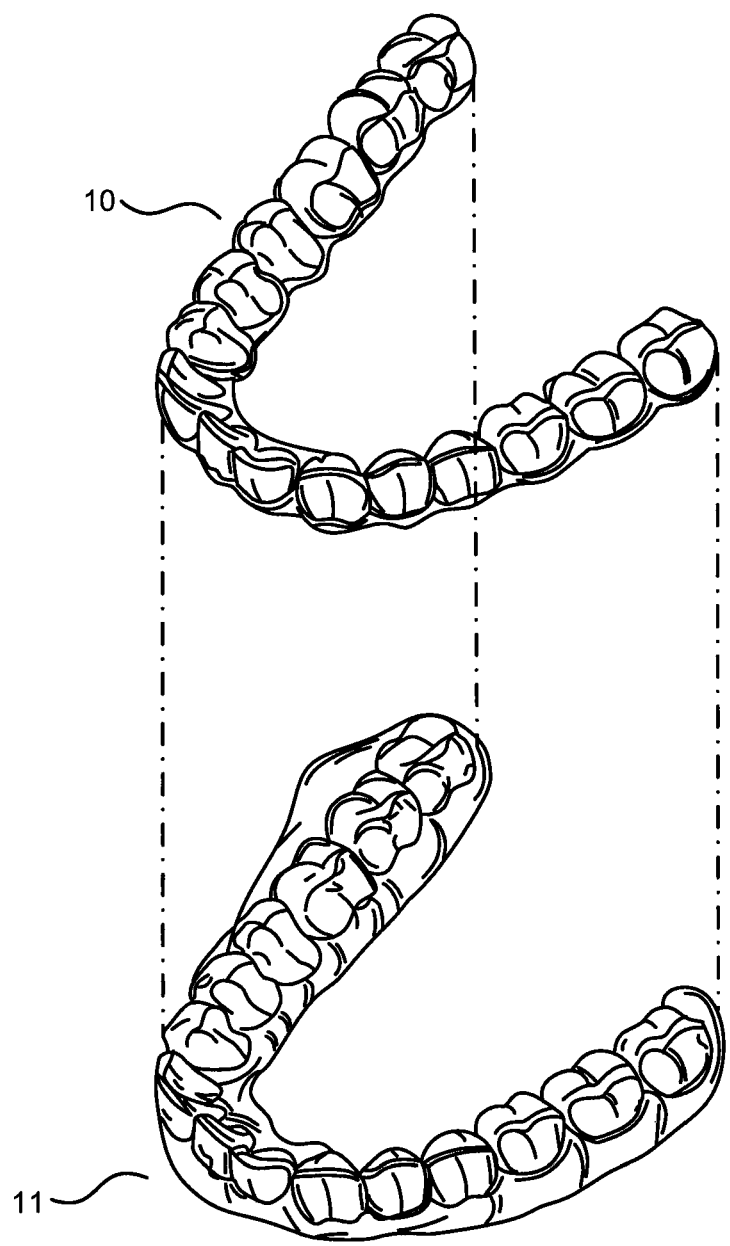
FIG. 1 illustrates a lower jaw and a patient removable orthodontic tooth positioning appliance.

FIG. 1 shows generally an exemplary patient removable orthodontic tooth positioning appliance 10 which is worn by a patient in order to restrain and/or reposition the patient's teeth (e.g., teeth as illustrated in jaw 11). The appliance may comprise a shell (e.g., a polymeric shell) having a plurality of teeth-receiving cavities that are shaped to receive and apply a resilient positioning force for restraining and/or repositioning the teeth. In one embodiment, a polymeric appliance can be formed from a thin sheet of suitable elastomeric polymeric material, such as Tru-Train (e.g., 0.03 inch) thermal forming dental material (Tru-Train Plastics, Rochester, Minn.). An appliance can fit over all teeth present in an upper or lower jaw, or less then all of the teeth. In some cases, only certain teeth received by an appliance will be repositioned by the appliance while other teeth can provide a base or anchor region for holding the appliance in place as it applies force against the tooth or teeth targeted for repositioning. In some cases, many or most, and even all, of the teeth will be repositioned at some point during treatment. Teeth which are engaged can also serve as a base or anchor for holding the appliance as it is worn by the patient. In some instances, no wires or other means will be provided for holding an appliance in place over the teeth. In some cases, however, it may be desirable or necessary to provide individual anchors on teeth with corresponding receptacles or apertures in the appliance so that the appliance can apply a selected force on the tooth. Exemplary appliances, including those utilized in the Invisalign® System, are described in numerous patents and patent applications assigned to Align Technology, Inc. including, for example in U.S. Pat. Nos. 6,450,807, and 5,975,893, which are incorporated by reference herein in their entirety, as well as on the company's website, which is accessible on the World Wide Web (see, e.g., the url "align.com").

An appliance can be designed and/or provided as part of a set or plurality of appliances. Appliances making use of tactile objects, as described herein, may constitute one or more appliances of a plurality. In such an embodiment, each appliance may be configured so a tooth receiving cavity has a geometry corresponding to an intermediate or final tooth arrangement intended for the appliance. The patient's teeth are progressively repositioned from their initial tooth arrangement to a final tooth arrangement by placing a series of incremental position adjustment appliances over the patient's teeth. The adjustment appliances can be generated all at the same stage or in sets or batches, e.g., at the beginning of a stage of the treatment, and the patient wears each appliance until the pressure of each appliance on the teeth can no longer be felt or has resulted in the maximum allowable tooth movement for that given stage. A plurality of different appliances (e.g., a set) can be designed and even fabricated prior to the patient wearing any appliance of the plurality. After wearing an appliance for an appropriate period of time, the patient replaces the current appliance with the next appliance in the series until no more appliances remain. The appliances are generally not affixed to the teeth and the patient may place and replace the appliances at any time during the procedure; i.e., patient removable appliances. The final appliance or several appliances in the series may have a geometry or geometries selected to overcorrect the tooth arrangement; i.e., have a geometry which would (if fully achieved) move individual teeth beyond the tooth arrangement which has been selected as the "final." Such over-correction may be desirable in order to offset potential relapse after the repositioning method has been terminated; i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

Figure 2:
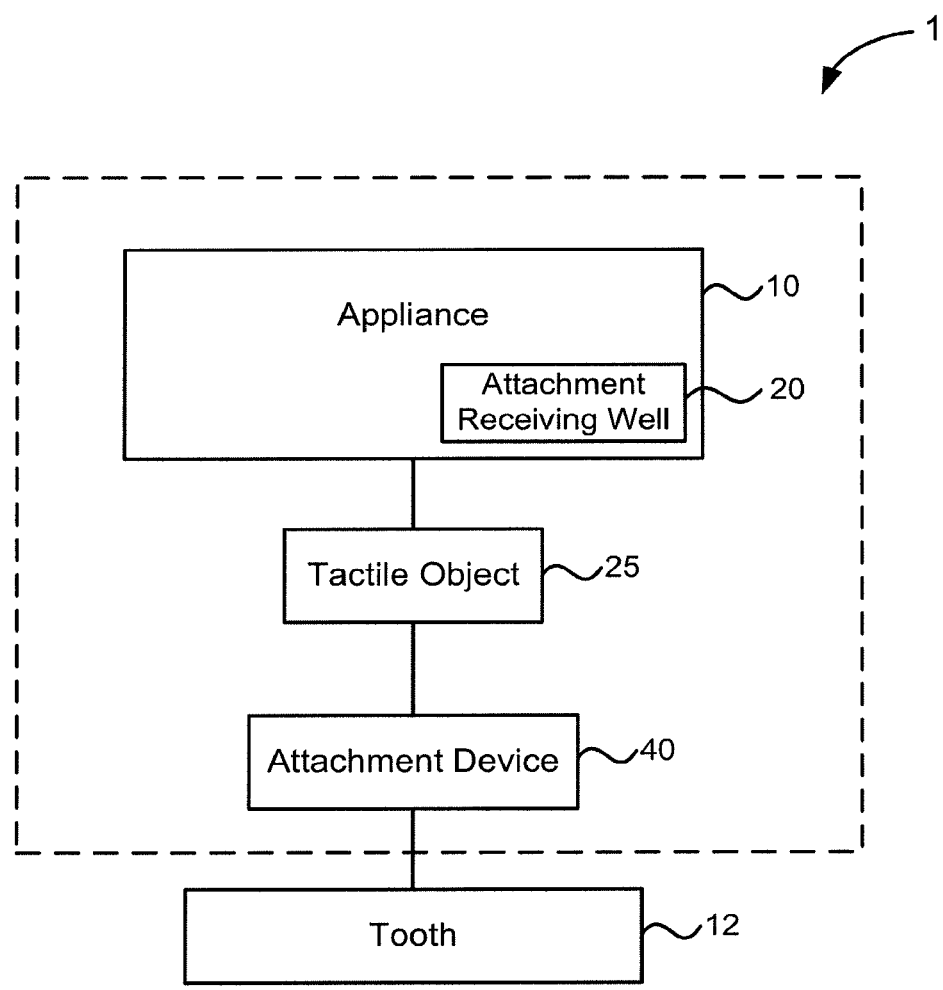
FIG. 2 illustrates a system for orthodontically positioning or repositioning a patient's tooth.

Referring now to FIG. 2, a system 1 for orthodontically positioning or repositioning a patient's tooth 12 is illustrated. The system 1 includes an orthodontic appliance 10 such as that illustrated in FIG. 1 is provided. The appliance 10 may have one or more attachment receiving wells 20 for receiving an attachment device 40 provided on an object such as a tooth 12. The system 1 further includes a tactile object 25 for modulating an engagement between the attachment device 40 and an attachment receiving well 20. As a result of modulating such an engagement, the fit between the attachment device 40 and the appliance 10 may be effected (e.g., increase quality of fit), and thus an operative affect of the attachment device 40 (e.g., force application) may be effected or improved.

The tactile object 25 may be provided between the attachment device 40 and the attachment receiving well 20. The tactile object 25 may be provided proximate to the attachment device 40. For example, the tactile object 25 may be disposed on or near all or portions of a surface of the attachment device 40. The tactile object 25 may also be provided proximate to an attachment receiving well 20. For example, the tactile object 25 may be disposed on or near all or portions of a surface of the attachment receiving well 20. The tactile object 25 may be disposed on or near both the attachment device 40 and the attachment receiving well 20. The tactile object 25 may be disposed in or near one or more inner wells of the attachment receiving well 20.

As a result of providing a tactile object 25, a working range of the appliance 10 may be increased since the appliance 10 can, via the tactile object 25, adapt itself to erroneous shapes and positions of the attachment device 40. In the case that the tactile object 25 has an elasticity or malleability greater than a corresponding elasticity or malleability of the appliance 10, a stress relaxation effect of the appliance 10 may be reduced since an elastic property of the tactile object 25 may apply a constant force for engaging the attachment 40 with the appliance 10. Moreover, the parameters of the tactile object 25 and an elastic modulus of the tactile object 25 can be selected to obtain a desired force magnitude on the tooth 12.

Figure 3A:
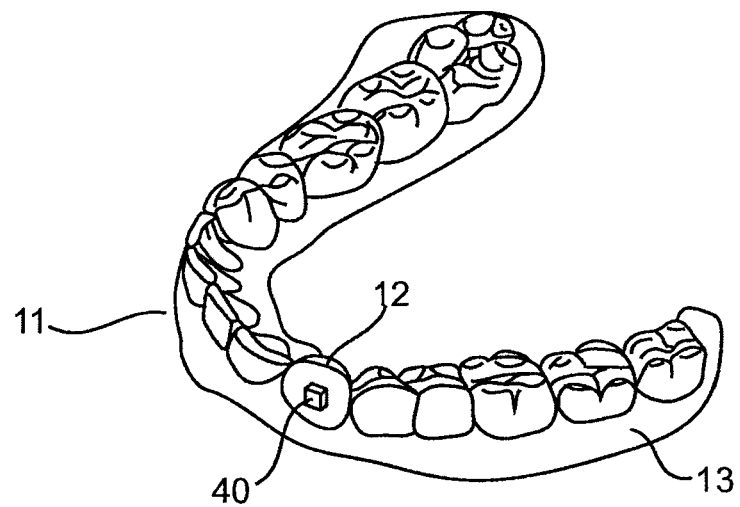
FIG. 3A illustrates a lower jaw having an attachment device coupled to a tooth.
Figure 3B:
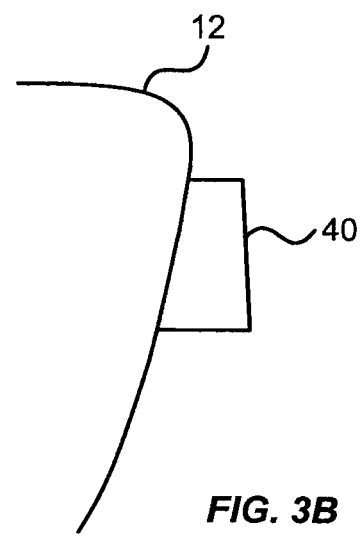
FIG. 3B illustrates an attachment device coupled to a tooth.

FIG. 3A and FIG. 3B illustrate an attachment device 40 bonded to a tooth 12 above a gingiva 13 of the lower jaw 11. The attachment device 40 may have any variety of geometries, including, e.g., having a cross-section in the shape of a rectangle, square, circle, and the like. The attachment device 40 may be directly bonded to the tooth 12, or may be coupled to the tooth 12 via an attachment body. Other attachment mechanisms may be used as well, including adhesives, flexible bands or connecting ligatures. The attachment device 40 may be bonded to any surface of a dental feature and may be provided in one or more locations. Specific shapes and designs may be particularly useful for certain locations. For example, attachment devices positioned on the lingual/buccal surfaces of the teeth would characteristically prevent irritation to contacting tissues, such as the tongue/cheek. The attachment device 40 engages the appliance 10 to effect a movement of a tooth 12 to which the attachment device 40 is secured. The attachment device 40 may also or alternatively engage the appliance 10 to effect a movement of one or more teeth other than a tooth 12 to which the attachment device 40 is secured. Exemplary attachment devices that can be utilized or modified for use in conjunction with tactile objects as described herein, are generally described in numerous patents and patent applications assigned to Align Technology, Inc. including, for example, U.S. Pat. Nos. 7,059,850 and 7,125,248, which are incorporated by reference herein in their entirety.

Figure 4A:
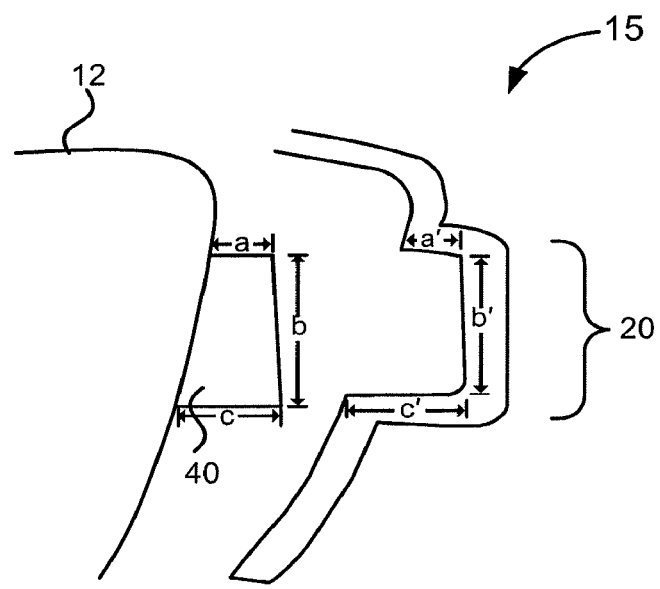
FIG. 4A illustrates an attachment device and an appliance according to an embodiment.

FIG. 4A is a cross-sectional view of an attachment device 40 coupled to a tooth 12 and a cross-section of a corresponding tooth receiving cavity 15 of an appliance 10. The tooth receiving cavity 15 includes an attachment receiving well 20 for receiving the attachment 40. According to an embodiment, the attachment 40 is made of a malleable material such as rubber, elastic, and the like, and has at least one dimension that is larger than a dimension of the attachment receiving well 20. The elasticity or malleability of the attachment 40 may be greater than a corresponding elasticity or malleability of the appliance 10.

The attachment 40 may have four dimensions, where only three are illustrated in FIG. 4A. A first dimension, a, corresponds to a length of a top surface of the attachment 40. A second dimension, b, corresponds to a height of a front surface of the attachment 40. A third dimension, c, corresponds to a length of a bottom surface of the attachment 40. A fourth dimension, not shown, corresponds to a width of the top, front, and bottom surfaces. The attachment receiving well 20 may have four corresponding dimensions, where only three are illustrated in FIG. 4A. A first dimension, a', corresponds to an upper surface for contacting the top surface of the attachment 40. A second dimension, b', corresponds to an inner surface for contacting the front surface of the attachment 40. A third dimension, c', corresponds to a lower surface for contacting the bottom surface of the attachment 40. A fourth dimension, not shown, is also for contacting the front surface of the attachment 40.

In an embodiment, one or more of the dimensions a, b, and c of the attachment 40 are larger than the corresponding dimensions a', b', and c' of the attachment receiving well 20. In another embodiment, all of the dimensions of the attachment 40 are larger than the corresponding dimensions of the attachment receiving well 20. For example, dimensions a, b, and c may be equal to 0.5 mm, 3 mm, and 1.5 mm, respectively, while dimensions a', b', and c' may be equal to 0.25 mm, 2.5 mm, and 1 mm, respectively.

As previously discussed, attachments may in some instances be less than optimally formed or placed, or otherwise result in less than optimal engagement or misalignment between the attachment and the appliance. Embodiments of the present invention may advantageously minimize or reduce the unwanted force delivery and/or engagement effects due to less than optimal formation and/or placement. For example, fabricating the attachment 40 including a material that has a greater malleability than that of the appliance 10 and at least one dimension larger than a corresponding dimension of the attachment receiving well 20 may modulate an engagement between the attachment 40 and the attachment receiving well 20. In particular, a better engagement may result because the malleability of the attachment 40 will provide some give and take. Moreover, appliances 10 are often very stiff, making it difficult for the appliance 10 to lock around attachment devices 40. Using a malleable, larger-sized attachment device 40 may advantageously increase a locking between the attachment device 40 and the appliance 10. As a result, the quality of a fit between the attachment 40 and the attachment receiving well 20 may be increased and thus an affect of the attachment 40 may be increased.

According to another embodiment, the attachment 40 is made of a malleable material such as rubber, elastic, and the like, and has all dimensions smaller than corresponding dimensions of the attachment receiving well 20. For example, the dimensions a, b, and c of the attachment 40, as well as the previously discussed dimension not illustrated, may all be smaller than the corresponding dimensions of the attachment receiving well 20. In this case, a locking between the attachment device 40 and the appliance 10 may be advantageously increased when a misalignment exists between the attachment 40 and the appliance 10 due to the give and take of the malleable material. As a result, the quality of a fit between the attachment 40 and the attachment receiving well 20 may be increased and thus an affect of the attachment 40 may be increased.

Figure 4B:
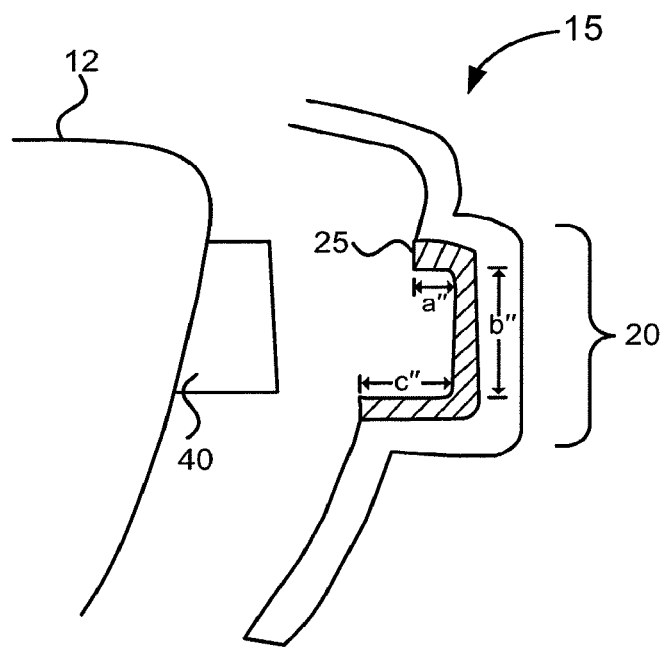
FIG. 4B illustrates an attachment device, appliance, and tactile object according to a first embodiment.

FIG. 4B is a cross-sectional view of an attachment device 40 coupled to a tooth 12 and a cross-section of a corresponding tooth receiving cavity 15 of an appliance 10. The tooth receiving cavity 15 includes an attachment receiving well 20. A tactile object 25 is disposed proximate the attachment receiving well 20. The tactile object 25 may be made of a malleable material such as elastic, rubber, and the like and may have an elasticity or malleability greater than a corresponding elasticity or malleability of both the appliance 10 and the attachment 40. The tactile object 25 may comprise a layer of material that covers an entire inner surface of the attachment receiving well 20 and has a predetermined thickness. The tactile object 25 may be formed in the shape of the attachment receiving well 20 and for receiving the attachment device 40. The attachment device 40 may be made of nonmalleable material, such as metal, ceramic, composite, and the like. The attachment device 40 may also be made of malleable material, such as elastic, rubber, and the like, as discussed above with respect to FIG. 4A.

In an embodiment, the attachment receiving well 20 has dimensions such as dimensions a', b', and c', equal to the corresponding dimensions of the attachment device 40, such as dimensions a, b, and c. In this case, the corresponding inner-surface dimensions of the tactile object 25, such as a", b", and c", may be less than the corresponding dimensions of the attachment device 40. In another embodiment, the attachment receiving well 20 and tactile object 25 are formed such that one or more of the inner-surface dimensions of the tactile object 25 are equal to or smaller than corresponding one or more dimensions of the attachment device 40. In a further embodiment, the attachment receiving well 20 and tactile object 25 are formed such that one or more of the inner-surface dimensions of the tactile object 25 are greater than corresponding one or more dimensions of the attachment device 40.

As previously discussed, attachments may be poorly formed or poorly placed, resulting in misalignment between the attachment and the appliance. However, placing a tactile object 25 proximate the attachment receiving well 20 may modulate an engagement between the attachment 40 and the attachment receiving well 20. In particular, a better engagement may result because the malleability of the tactile object 25 will provide some give and take and possibly help direct the force applied by the attachment 40. Moreover, appliances 10 are often very stiff, making it difficult for the appliance 10 to lock around attachment devices 40. Using a malleable tactile object 25 may advantageously increase a locking between the attachment device 40 and the appliance 10. As a result, the quality of a fit between the attachment 40 and the attachment receiving well 20 may be increased and thus an affect of the attachment 40 may be increased.

Figure 4C:
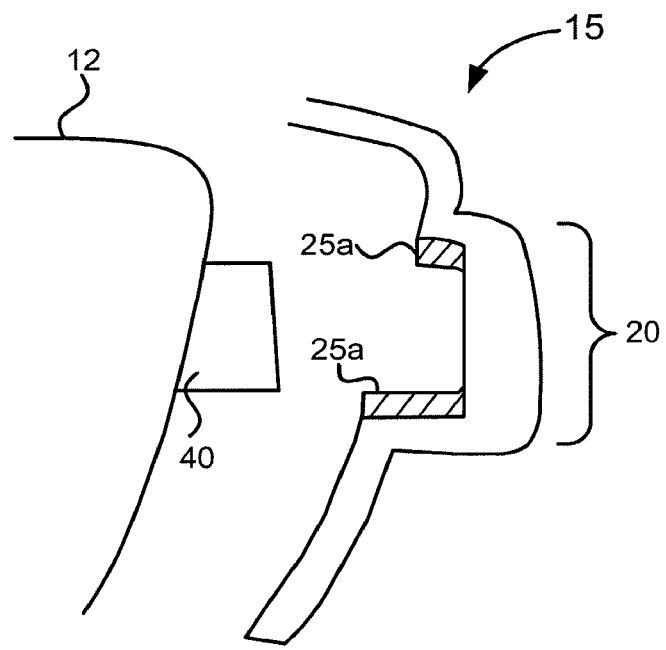
FIG. 4C illustrates an attachment device, appliance, and tactile object according to a second embodiment.

FIG. 4C is a cross-sectional view of an attachment device 40 coupled to a tooth 12 and a cross-section of a corresponding tooth receiving cavity 15 of an appliance 10. The tooth receiving cavity 15 includes an attachment receiving well 20. The tactile object 25a provided in this embodiment is similar to that illustrated in FIG. 4B, except in this embodiment the tactile object 25a only covers portions of the inner surface of the attachment receiving well 20. For example, the tactile object 25a may cover an upper surface of the attachment receiving well 20 for contacting the top surface of the attachment 40 and/or a lower surface of the attachment receiving well 20 for contacting the bottom surface of the attachment 40. Various relative sizes of the attachment device 40 and a resulting space in the attachment receiving well 20 for receiving the attachment device 40 are possible, as described above with respect to FIG. 4B.

Figure 4D:
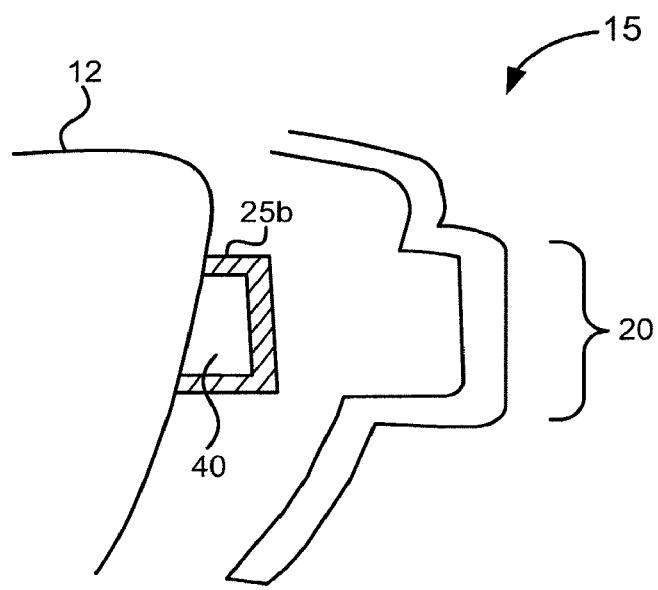
FIG. 4D illustrates an attachment device, appliance, and tactile object according to a third embodiment.

FIG. 4D is a cross-sectional view of an attachment device 40 coupled to a tooth 12 and a cross-section of a corresponding tooth receiving cavity 15 of an appliance. A tactile object 25b is provided proximate the attachment device 40. The tooth receiving cavity 15 includes an attachment receiving well 20. The tactile object 25b in this embodiment is similar to that illustrated in FIG. 4B, except in this embodiment the tactile object 25b covers all exposed surfaces of the attachment device 40. In other words, the tactile object 25b covers all surfaces of the attachment device 40 except for a surface of the attachment device 40 bonded to the tooth 12. Various relative sizes of the attachment receiving well 20 and the combined attachment device 40 and tactile object 25b are possible, as discussed above with respect to FIG. 4B.

Figure 4E:
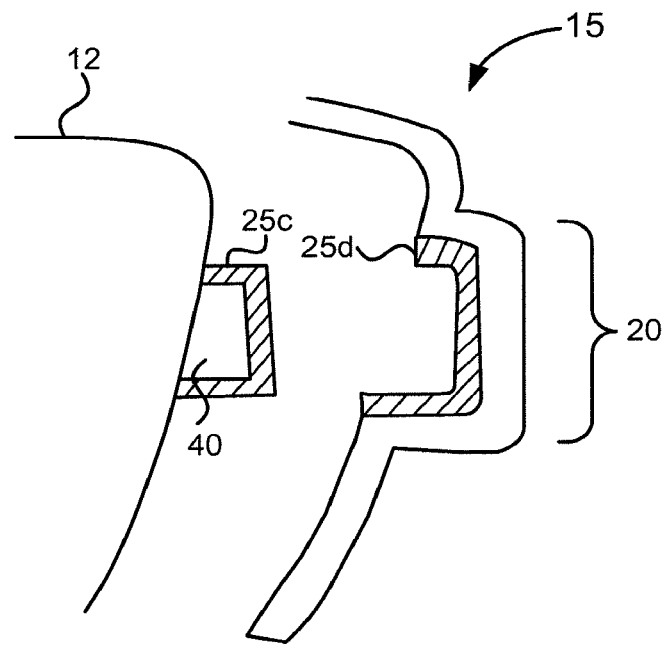
FIG. 4E illustrates an attachment device, appliance, and tactile object according to a fourth embodiment.

FIG. 4E is a cross-sectional view of an attachment device 40 coupled to a tooth 12 and a cross-section of a corresponding tooth receiving cavity 15 of an appliance 10. The tooth receiving cavity 15 includes an attachment receiving well 20 for receiving the attachment 40. A portion of a tactile object 25c covers an entire surface of the attachment 40, and a portion of the tactile object 25d covers an entire inner surface of the attachment receiving well 20. The portions may be made of the same or different material, and have the same or different malleability. Various relative sizes of a resulting space in the attachment receiving well 20 for receiving the attachment device 40 and the combined attachment device 40 and attached portion of the tactile object 25c are possible, as described above with respect to FIG. 4B.

Figure 4F:
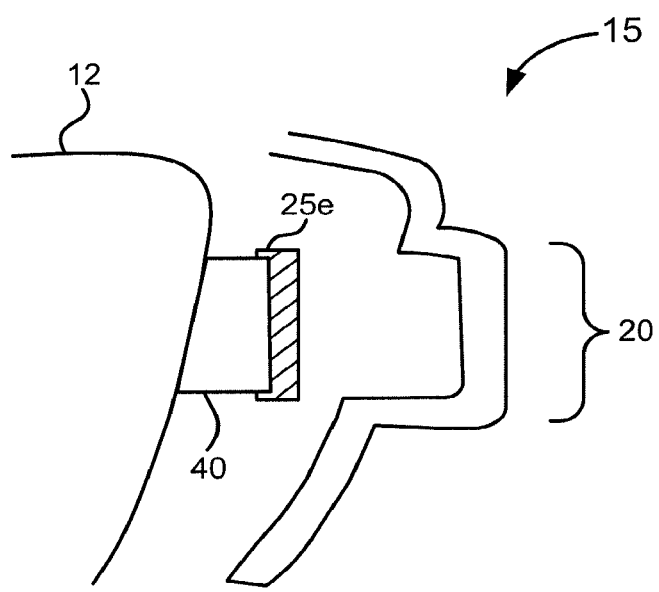
FIG. 4F illustrates an attachment device, appliance, and tactile object according to a fifth embodiment.

FIG. 4F is a cross-sectional view of an attachment device 40 coupled to a tooth 12 and a cross-section of a corresponding tooth receiving cavity 15 of an appliance 10. A tactile object 25e is provided proximate the attachment device 40. The tooth receiving cavity 15 includes an attachment receiving well 20. The tactile object 25e in this embodiment is similar to that illustrated in FIG. 4B, except in this embodiment the tactile object 25e covers only a portion of one or more exposed surfaces of the attachment device 40. In other words, the tactile object 25e covers a portion of at least one surface of the attachment device 40 except for a surface of the attachment device 40 bonded to the tooth 12. Various relative sizes of the attachment receiving well 20 and the combined attachment device 40 and tactile object 25e are possible, as discussed above with respect to FIG. 4B.

FIG. 5A is a cross-sectional view of an attachment device 40 coupled to a tooth 12 and a cross-section of a corresponding tooth receiving cavity 15 of an appliance 10. The tooth receiving cavity 15 includes an attachment receiving well 20. A tactile object 25f is provided proximate the attachment receiving well 20. FIG. 5B illustrates a magnified portion of the tactile object 25f and a portion of the appliance 10. The tactile object 25f may be made of malleable material such as elastic, rubber, and the like. In an embodiment, the tactile object 25f is bonded to and extends from an inner surface of the tooth receiving cavity 15 and has a predetermined shape. The tactile object 25f may be formed in the shape of an elongated body, a rectangular cube, a square cube, a cylinder, and the like. The predetermined shape may be much smaller than that illustrated in FIG. 5A and FIG. 5B. The tactile object 25f may be bonded to an inner surface of the attachment receiving well 20 as illustrated in FIG. 5A. The tactile object 25f may also be bonded to other surfaces of the attachment receiving well 20 or the tooth receiving cavity 15, including an upper surface of the attachment receiving well 20 for contacting the top surface of the attachment 40 and a lower surface of the attachment receiving well 20 for contacting the bottom surface of the attachment 40. The tactile object 25f may also be bonded to other surfaces of the appliance 10, including surfaces provided outside the attachment receiving well 20.

FIG. 5C is a cross-sectional view of an attachment device 40 coupled to a tooth 12 and a cross-section of a corresponding tooth receiving cavity 15 of an appliance 10. The tooth receiving cavity 15 includes an attachment receiving well 20. A tactile object 25g is provided proximate the attachment receiving well 20. FIG. 5D illustrates a magnified portion of the tactile object 25g and a portion of the appliance 10. The tactile object 25g in this embodiment is similar to that illustrated in FIG. 5A and FIG. 5B, except that in this embodiment the tactile object 25g comprises a plurality of portions that are bonded to and extend from an inner surface of the tooth receiving cavity 15. The plurality of portions may all be bonded to the same surface or to different surfaces of the tooth receiving cavity 15. The plurality of portions may be made of the same or different material, and may have the same or different dimensions.

FIG. 5E is a cross-sectional view of an attachment device 40 coupled to a tooth 12, and a cross-section of a corresponding tooth receiving cavity 15 of an appliance 10. The tooth receiving cavity 15 includes an attachment receiving well 20. A tactile object 25h and a base 27 are provided proximate the attachment receiving well 20. FIG. 5F illustrates a magnified portion of the tactile object 25h, base 27, and a portion of the appliance 10. The embodiment illustrated in FIG. 5E and FIG. 5F is the same as that illustrated in FIG. 5A and FIG. 5B, except for the provision of a base 27. The base 27 may be formed in an inner well of the attachment receiving well 20. The base 27 may be made of the same material or different material than the tactile object 25h, and the base 27 may have the same or different malleability as that the tactile object 25h. The base 27 may be made of the same or different material than the appliance 10. The base 27 may be physically coupled to the tactile object 25h, by either a bonding the base 27 to the tactile object 25h or forming the base 27 and the tactile object 25h as a single unit. In an embodiment, the base 27 is made of material that has a greater elasticity or malleability than a corresponding elasticity or malleability of the appliance 10.

The tactile object 25h and the base 27 may be fabricated together as one unit or separate from one another. In an embodiment, the appliance 10 is formed to include an inner well in the attachment receiving well 20, and the tactile object 25h and base 27 are subsequently inserted into the inner well. The tactile object 25h may be bonded to the base 27 or formed together with the base 27 as one unit before being placed into the well. The base 27 may be made of malleable material such as rubber, elastic, and the like. The parameters of the base 27 such as and an elastic modulus of the base 27 and/or a size of the base 27 can be selected to obtain a desired force magnitude on the tooth 12. In an embodiment, the base 27 has a greater elasticity or malleability than the tactile object 25h. As a result, a local elasticity or malleability at the base 27 can be more tolerant to error in shapes and position of the attachment 40. A shape and size of the tactile object 25h and the base 27 may be standardized for different treatment conditions.

FIG. 5G is a cross-sectional view of an attachment device 40 coupled to a tooth 12 and a cross-section of a corresponding tooth receiving cavity 15 of an appliance 10. The tooth receiving cavity 15 includes an attachment receiving well 20 and a deflected portion 29. A tactile object 25i and a base 27 are provided proximate the attachment receiving well 20. FIG. 5H illustrates a magnified portion of the tactile object 25*i*, base 27, a portion of the appliance 10, and a deflected portion 29 of the appliance 10. The embodiment illustrated in FIG. 5G and FIG. 5H is the same as that illustrated in FIG. 5E and FIG. 5F, except for the provision of a deflected portion 29. The deflected portion 29 is a portion of the appliance 10 which expands outwardly from a surface of the appliance 10. The deflected portion 29 may form as a result of fabricating the appliance 10 to include an inner well within the attachment receiving well 20.

FIG. 5I is a cross-sectional view of an attachment device 40 coupled to a tooth 12 and a cross-section of a corresponding tooth receiving cavity 15 of an appliance 10. The tooth receiving cavity 15 includes an attachment receiving well 20. A tactile object 25*j* and a base 27 are provided proximate the attachment receiving well 20. FIG. 5J illustrates a magnified portion of the tactile object 25*j*, base 27, and a portion of the appliance 10. The embodiment illustrated in FIG. 5I and FIG. 5J is the same as that illustrated in FIG. 5E and FIG. 5F, except for a size of the base 27. The base 27 according to this embodiment may have an exposed surface area larger than the surface area at an end of the tactile object 25*j* proximate the tooth receiving cavity 15. The base 27 may cover an entire exposed surface of the attachment receiving well 20 or only portions of an exposed surface of the attachment receiving well 20. The base 27 may be continuous or discontinuous.

FIG. 5K is a cross-sectional view of an attachment device 40 coupled to a tooth 12 and a cross-section of a corresponding tooth receiving cavity 15 of an appliance 10. The tooth receiving cavity 15 includes an attachment receiving well 20. A tactile object 25*k* and a base 27 are provided proximate the attachment receiving well 20. FIG. 5L illustrates a magnified portion of the tactile object 25*k*, base 27, and a portion of the appliance 10. The embodiment illustrated in FIG. 5K and FIG. 5L is the same as that illustrated in FIG. 5I and FIG. 5J except that the tactile object 25*k* comprises a plurality of portions similar to those described above with respect to FIG. 5C and FIG. 5D.

FIG. 5M is a cross-sectional view of an attachment device 40 coupled to a tooth 12 and a cross-section of a corresponding tooth receiving cavity 15 of an appliance 10. The tooth receiving cavity 15 includes an attachment receiving well 20 and a deflected portion 29. A tactile object 25*e* is provided proximate the attachment 40, and a tactile object 25*m* and a base 27 are provided proximate the attachment receiving well 20. FIG. 5N illustrates a magnified portion of the tactile object 25*m*, base 27, deflected portion 29 of the appliance 10, and a portion of the appliance 10. The embodiment illustrated in FIG. 5M and FIG. 5N is the same as that illustrated in FIG. 5G and FIG. 5H except for the tactile object 25*l* covering the attachment 40. The tactile object 25*m* covering the attachment 40 may be the same as that illustrated in FIG. 4D.

FIG. 5O is a cross-sectional view of an attachment device 40 coupled to a tooth 12 and a cross-section of a corresponding tooth receiving cavity 15 of an appliance 10. The tooth receiving cavity 15 includes an attachment receiving well 20 and a deflected portion 29. A tactile object 25*n* is provided proximate the attachment 40. A tactile object 25*o*, 25*p* and a base 27 are provided proximate the attachment receiving well 20. FIG. 5P illustrates a magnified portion of each of the tactile object 25, base 27, deflected portion 29 of the appliance 10, and the appliance 10. The embodiment illustrated in FIG. 5O and FIG. 5P is a combination of the embodiments illustrated in at least FIG. 4C, FIG. 4F, FIG. 5G, and FIG. 5K. The tactile object 25*n*, 25*o*, 25*p* according to this embodiment may be made of the same or different material, and may have a same or different malleability. The base 27 according to this embodiment may have an exposed surface area larger than or equal to the surface area at an end of the tactile object 25 coupled to the tooth receiving cavity 15.

The arrangement of a tactile object is not limited to those embodiments illustrated in FIG. 4A to FIG. 5P. Rather, various combinations of these embodiments are possible.

FIG. 5Q and FIG. 5R illustrate an operation of a tactile object 25*q* further described in accordance with FIGS. 5E and 5F. According to an embodiment, the tactile object 25*q* has an elasticity or malleability greater than a corresponding elasticity or malleability of an attachment 40 and an appliance 10. A misalignment exists between the attachment 40 and the attachment receiving well 20. Upon application of the appliance 10 to the tooth 12, the attachment receiving well 20 imperfectly receives the attachment 40. As a result of inserting the attachment 40 into the attachment receiving well 20, the tactile object 25*q* is deflected. The tactile object 25*q* displaces much more easily than the appliance 10 since the elasticity or malleability of the tactile object 25*q* is greater than a corresponding elasticity or malleability of the appliance 10. A reciprocal force applied by the tactile object 25*q* onto the attachment 40 due to the elasticity or malleability of the tactile object 25*q* advantageously reduces an amount of relative motion between the attachment 40 and the attachment receiving well 20. The reciprocal force will have a magnitude mostly determined by the deformation of the tactile object 25*q* and a direction which returns the tactile object 25*q* to a resting state. Accordingly, the tactile object 25*q* modules an engagement between the attachment 40 and attachment receiving. As a result, the quality of a fit between the attachment 40 and the attachment receiving well 20 may be increased and thus an affect of the attachment 40 may be increased.

According to another embodiment, the base 27 has an elasticity or malleability greater than a corresponding elasticity or malleability of an attachment 40, an appliance 10, and the tactile object 25*q*. As a result of inserting the attachment 40 into the attachment receiving well 20, the tactile object 25*q* is deflected. A reciprocal force is applied by the tactile object 25*q* onto the attachment 40. However, according to this embodiment, the reciprocal force is primarily generated due to the elasticity or malleability of the base 27 and will have a magnitude mostly determined by the deformation of the base 27 and a direction which returns the base 27 to a resting state. The tactile object 25*q* displaces much more easily than the appliance 10 since the elasticity or malleability of the base 27 is greater than a corresponding elasticity or malleability of the appliance 10. Accordingly, the tactile object 25*q* modules an engagement between the attachment 40 and attachment receiving. As a result, the quality of a fit between the attachment 40 and the attachment receiving well 20 may be increased and thus an affect of the attachment 40 may be increased.

FIG. 5S and FIG. 5T illustrate an operation of a tactile object 25 further described in accordance with FIG. 5K and FIG. 5L. The operation of the tactile object 25*r* is identical to that described above with respect to FIG. 5Q and FIG. 5R, except that the tactile object 25*r* comprises a plurality of portions in which some or all of the portions apply a reciprocal force to the attachment 40. The reciprocal force applied to the attachment 40 in this case will have a force magnitude and direction determined by a deflection of the majority of the portions of the tactile object 25*r* in contact with the attachment 40.

Figure 6A:
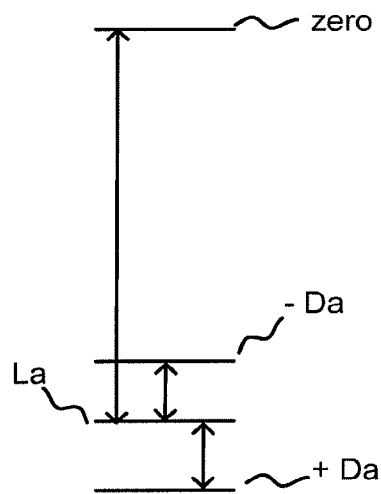
FIG. 6A illustrates distances of an attachment taken into account during formation of a tactile object.
Figure 6B:
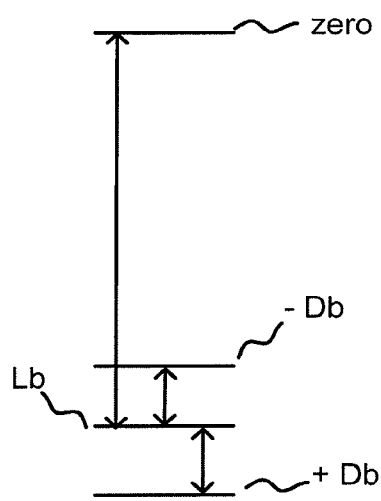
FIG. 6B illustrates distances of a tactile object taken into account during formation of a tactile object.

FIG. 6A illustrates distances of an attachment taken into account during formation of a tactile object. FIG. 6B illustrates distances of a tactile object taken into account during formation of the tactile object. During design of the attachment such as that illustrated in FIG. 3B, the attachment is positioned at a distance La from a zero reference located on a surface of the tooth. A manufacturing and bonding tolerance for the attachment is ±Da, where the bonding tolerance includes a tolerance for bonding performed by an optometrist. Accordingly, an actual position of the attachment from the surface of the tooth varies from (La−Da) to (La+Da). Similarly, for a tactile object such that illustrated in FIG. 5E and FIG. 5F, a manufacturing and bonding tolerance is ±Db, so that an actual position of the tactile object from a surface of the appliance varies from (Lb−Db) to (Lb+Db). Da is greater than Db since Da represents a combination of manufacturing and bonding tolerance whereas Db represents a manufacturing tolerance alone.

For some tooth movements, it is desired that a force be applied at a surface of the attachment; i.e., at the distance La. In an embodiment where a single tactile object is used, such as that illustrated in FIG. 5E and FIG. 5F, a desirable manufacturing length of the tactile object is Lb=(La−Da). A deflection of the tactile object may be at least equal to 2Da. In an embodiment where a base is provided, the deflection may be provided primarily by the malleability of the base. In an embodiment where a base is not provided, the deflection may be provided primarily by the malleability of the tactile object.

In an embodiment where a tactile object having a plurality of portions is used, such as that illustrated in FIG. 5K and FIG. 5L, the plurality of portions may be smaller than when a single tactile object is used. An area on the appliance where the portions of the tactile object occupy may center at (La−Da) and be greater than 2Da in that dimension. When the appliance is engaged with the teeth, at least one of the portions of the tactile object may deflect and contact the attachment to generate a force in favor of tooth movement.

The aforementioned techniques for manufacturing tactile objects do not only apply to situations where a single tactile object such as that illustrated in FIG. 5E and FIG. 5F and a tactile object having a plurality of portions as illustrated in FIG. 5K and FIG. 5L are used. Rather, these techniques similarly apply to other situations where a tactile object is used as described herein.

Figure 7A:
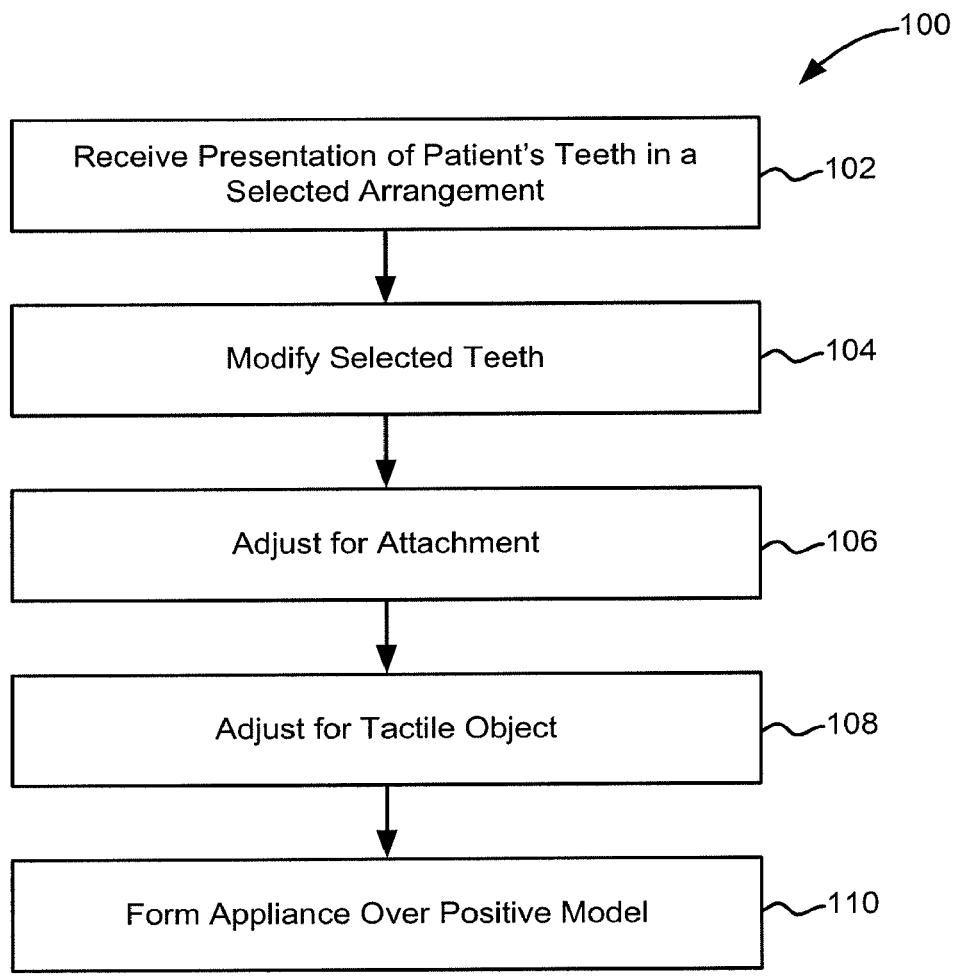
FIG. 7A illustrates a method for forming an appliance according to a first embodiment.

FIG. 7A illustrates a method 100 for fabricating an appliance 10 according to a first embodiment. In step 102, a representation of a patient's teeth in a selected arrangement is received. The selected arrangement in particular, and the representation in general, will depend upon the purpose of the particular appliance 10 being defined. Where the appliance 10 will be used to apply positioning forces to constrain a patient's teeth in their current arrangement, the selected arrangement can correspond to the current arrangement of the patient's teeth. Where the appliance 10 will be used to apply repositioning forces to move the patient's teeth from their current arrangement toward a subsequent arrangement, the selected arrangement will typically deviate from the current arrangement of the patient's teeth.

In step 104, selected teeth of the received representation are optionally modified. This optional modification can include any number of the teeth, from one to all. A wide range of modifications are possible. For example, the size of any number of teeth can be scaled by a desired amount. The teeth in the representation can also be locally modified, by either adding or removing material.

In step 106, the received representation is optionally adjusted for an attachment 40. The optional adjustment can include adjustment for one or more attachments, where one or more attachments may be provided for a single tooth. Various adjustments are possible. For example, the representation may be adjusted to facilitate an attachment receiving well 20 in a tooth receiving cavity 15 of the appliance 10. As previously discussed in the context of a tactile object 25, the attachment receiving 20 well may have one or more dimensions smaller than, equal to, or larger than a corresponding attachment 40. Where the representation is a physical definition, the adjustment may be made by attaching a material to or forming a material on the representation, where a shape of the material is a negative of the desired adjustment. Where the representation is a digital definition, the adjustment may be a digital adjustment.

In step 108, the received representation is optionally adjusted for a tactile object 25. The optional adjustment can include adjustment for one or more tactile objects, where one or more tactile objects may be provided for a single tooth. Each tactile object may comprise one or a plurality of portions. For example, the representation may be adjusted to facilitate an attachment receiving well 20. As previously discussed in the context of a tactile object 25, the attachment receiving well 20 may have one or more dimensions smaller than, equal to, or larger than a corresponding attachment 40 based on an arrangement of a tactile object 25. The optional adjustment can also include adjustment for one or more bases 27, where one or more bases 27 may be provided for a single tooth 12. For example, the representation may be adjusted to facilitate an inner well within an attachment receiving well 20. The inner well may be the smaller than, the same size as, or larger than an attached tactile object 25. Where the representation is a physical definition, the adjustment may be made by attaching a material to or forming a material on the representation, where a shape of the material is a negative of the desired adjustment. Where the representation is a digital definition, the adjustment may be a digital adjustment.

In step 110, the appliance 10 can be fabricated by forming a sheet of polymeric material over a physical model/mold corresponding to the digital or physical definition resulting from steps 102 to 108.

Figure 7B:
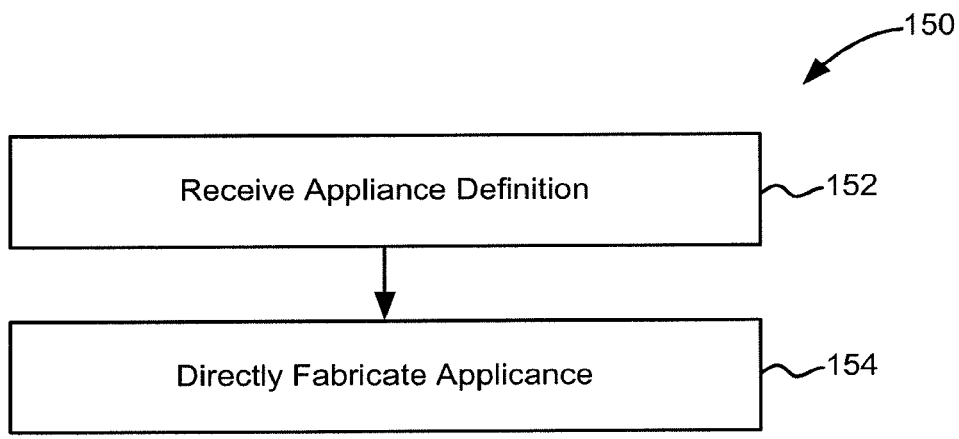
FIG. 7B shows a method for forming an appliance according to a second embodiment.

FIG. 7B shows a method 150 for fabricating an appliance 10 according to a second embodiment. In step 152, a digital definition of an appliance is received. The digital definition as received may include adjustments as described above in steps 106 and 108 with respect to FIG. 7A. Additionally or alternatively, the digital definition may be adjusted as described above in steps 106 and 108 after being received.

In step 154, an appliance 10 is directly fabricated using the digital definition from step 152. Various known manufacturing processes can be used to directly fabricate an appliance 10. In one approach, the appliance 10 is formed by a stereo-lithography fabrication machine, where resin is selectively hardened in the shape of the digital definition.

Figure 8A:
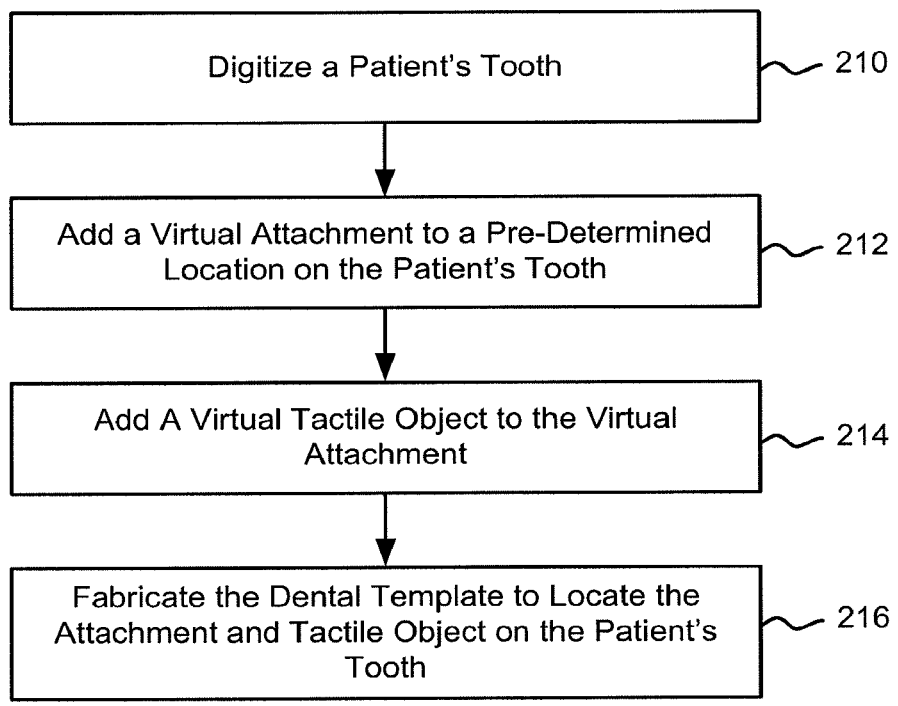
FIG. 8A shows a method for forming a dental template.

FIG. 8A shows a method for fabricating a dental template to position an attachment 40 and a tactile object 25 on a patient's tooth 12. In step 210, a patient's tooth 12 is digitized. Next, in step 212, a virtual representation of the attachment 40 is added to a pre-determined location on the digitized tooth. In step 214, a virtual representation of a tactile object 25 is added to the virtual representation of the attachment 40. The virtual representation of the tactile object 25 may cover all or portions of exposed surfaces of the virtual representation of the attachment 40. Finally, in step

214, a dental template is fabricated for locating the attachment 40 and the tactile object 25 on the patient's tooth 12.

Figure 8B:
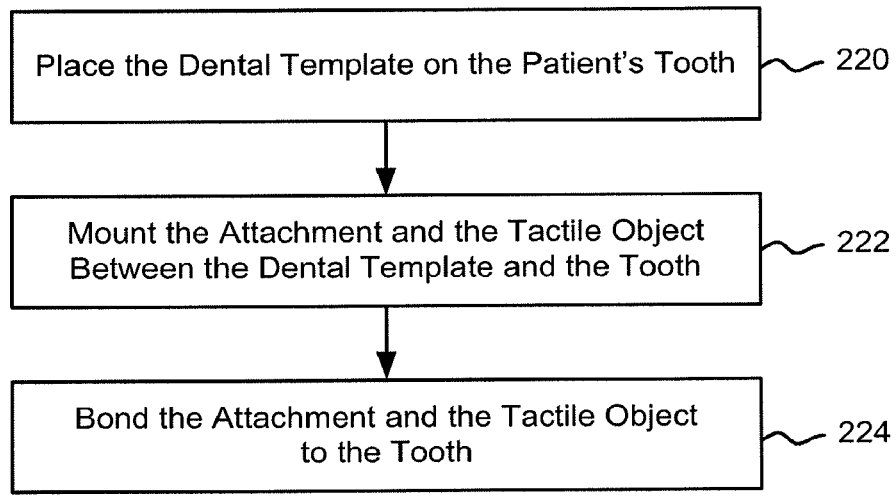
FIG. 8B shows a first method for placing an attachment and a tactile object on a patient's tooth.

FIG. 8B shows a first method for placing an attachment 40 and a tactile object 25 on a patient's tooth 12. The process uses a dental template such as that fabricated according to the method of FIG. 8A. The method includes a first step 220 of placing the dental template on the patient's tooth 12; a second step 222 of mounting the attachment 40 and the tactile object 25 between the dental template and the tooth 12; and a third step 224 of bonding the attachment 40 and the tactile object 25 to the tooth 12. In the bonding operation, chemical curing and/or light curing adhesives may be used.

In an embodiment, the tactile object 25 is bonded to the attachment 40 before the second step of mounting the attachment 40 and the tactile object 25 between the dental template and the tooth 12. In another embodiment, the tactile object 25 is not bonded to the attachment 40 before the second step of mounting the attachment 40 and the tactile object 25. In this case, the tactile object 25 may be bonded to the attachment 40 by the chemical and/or light curing of the third step 224.

Figure 8C:
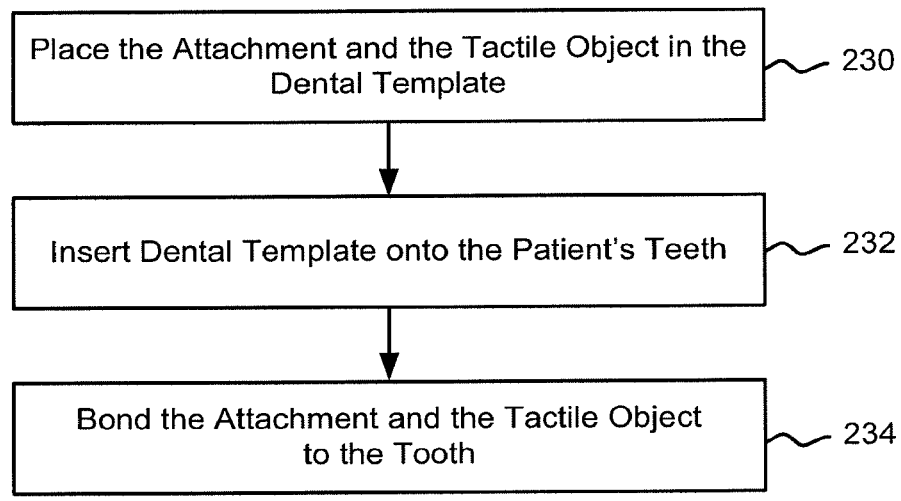
FIG. 8C shows a second method for placing an attachment on a patient's tooth.

FIG. 8C shows a second method for placing an attachment 40 and a tactile object 25 on a patient's tooth 12. According to this process, in a first step 230 the attachment 40 and tactile object 25 are placed in a dental template such as that fabricated according to the method of FIG. 8A. Next, in a second step 232, the dental template containing the attachment 40 and the tactile object 25 are inserted onto the patient's teeth. Finally, in a third step 234, the attachment 40 and the tactile object 25 are bonded to the tooth 12.

In an embodiment, the tactile object 25 is bonded to the attachment 40 before the first step of placing the attachment 40 and tactile object 25 in a dental template. In another embodiment, the tactile object 25 is not bonded to the attachment 40 before the first step of placing the attachment 40 and tactile object 25 in a dental template. In this case, the tactile object 25 may be bonded to the attachment 40 by the chemical and/or light curing of the third step 234.

According to an embodiment not illustrated, a method of forming an attachment 40 such as that illustrated in FIG. 4A is provided. In other words, a method of forming a malleable attachment 40 on a tooth 12 is provided. This method is the same as that illustrated in FIG. 8A, FIG. 8B, and/or FIG. 8C, except in this case a tactile object 25 is not provided. For example, step 214 may not be performed, and a dental template may be fabricated to only locate an attachment 40 (and not a tactile object 25) on a patient's tooth 12 in accordance with step 216. According to this embodiment, the attachment 40 formed has a greater malleability than an appliance 10 which receives the attachment 40. In this embodiment, a very low viscosity UV curable adhesive may be used to bond the attachment 40 to a surface of the tooth 12.

More information on the fabrication of orthodontic appliances, attachments, and dental templates is disclosed in U.S. Pat. Nos. 7,482,647, 7,481,647, 7,476,100, 7,435,084, 7,384,266, 7,357,636, 7,326,051, 7,331,783, 7,335,024, 7,125,248, 7,123,767, 7,110,594, 7,108,508, 7,059,850, 7,056,115, 7,037,111, 6,499,997, 6,497,574, 6,488,499, 6,485,298, 6,471,511, 6,463,344, 6,457,972, 6,454,565, 6,450,807, 6,409,504, 6,406,292, 6,398,548, 6,394,801, 6,390,812, 6,386,878, 6,386,864, 6,371,761, 6,318,994, 6,309,215, 6,299,440, 6,227,851, 6,227,850, 6,217,325, 6,210,162, and 5,975,893, the contents of which are hereby incorporated by reference.

Figure 9:
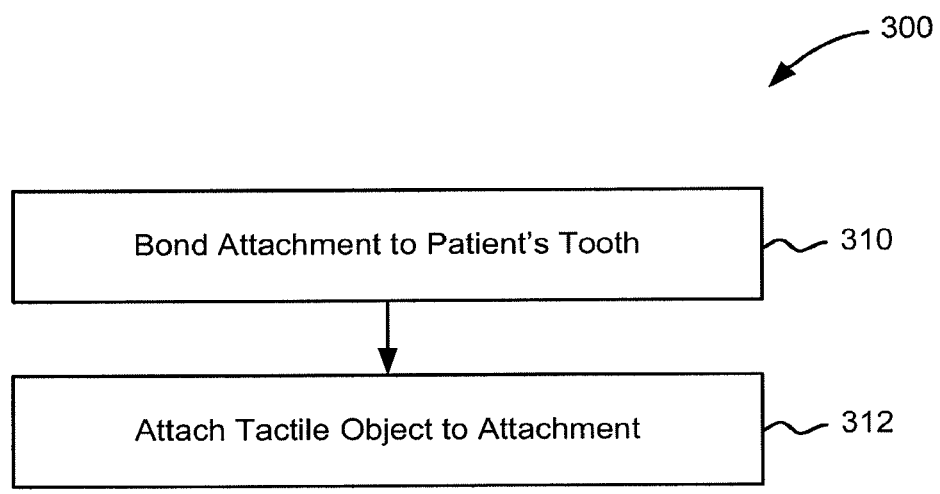
FIG. 9 shows a method for attaching a tactile object to a patient's tooth.

FIG. 9 shows a method for attaching a tactile object 25 to a patient's tooth 12. In step 310, an attachment 40 is bonded to the tooth 12. This bonding may be performed as described above in FIG. 8A, FIG. 8B, and FIG. 8C, except that the tactile object 25 is not incorporated into the steps illustrated in FIG. 8A, FIG. 8B, and FIG. 8C. In step 312, a tactile object 25 is attached to the attachment 40. The tactile object 25 may cover a portion of or a whole of an exposed surface of the attachment 40. The tactile object 25 may be attached to the attachment 40 via an adhesive, by elastic forces of the tactile object 25, and the like.

Figure 10A:
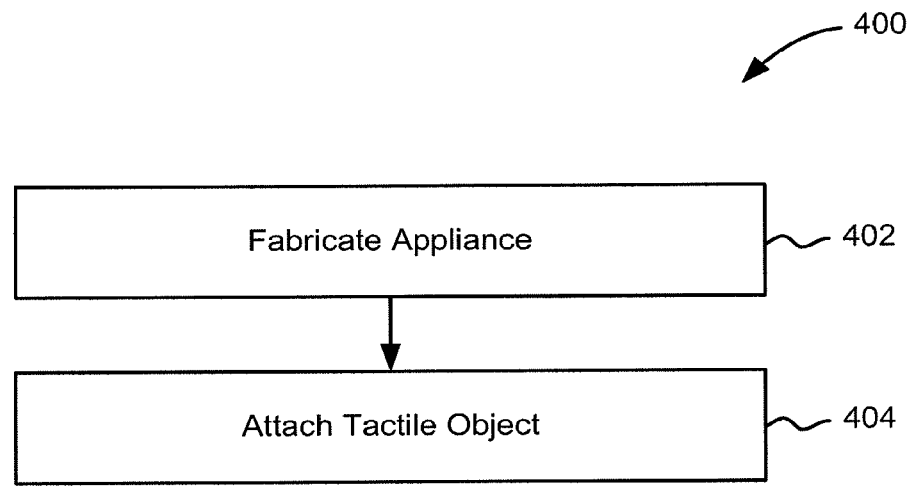
FIG. 10A shows a method for forming a tactile object on an appliance.

FIG. 10A shows a method for forming a tactile object 25 on an appliance 10. In step 402, an appliance 10 is formed. For example, the appliance 10 may be formed in accordance with one of the methods illustrated in FIG. 7A and FIG. 7B. In step 404, a tactile object 25 is attached to the appliance 10. In an embodiment, rubber is drip coated or spray coated on an inner surface of the appliance 10. For example, rubber may be drip coated or spray coated on an inner surface of an attachment receiving well 20 of the appliance 10. An automated dispensing system may be used to drip coat or spray coat the appliance. In this case, the area of the appliance 10 that will be rubber coated may first be laser-marked so that an automated dispending arm can locate the area to add the rubber material. In another embodiment, the tactile object 25 is pre-formed separate from the formation of the appliance 10. The tactile object 25 may then be bonded to a surface of the appliance 10 via an adhesive, by elastic forces of the tactile object 25, and the like.

Figure 10B:
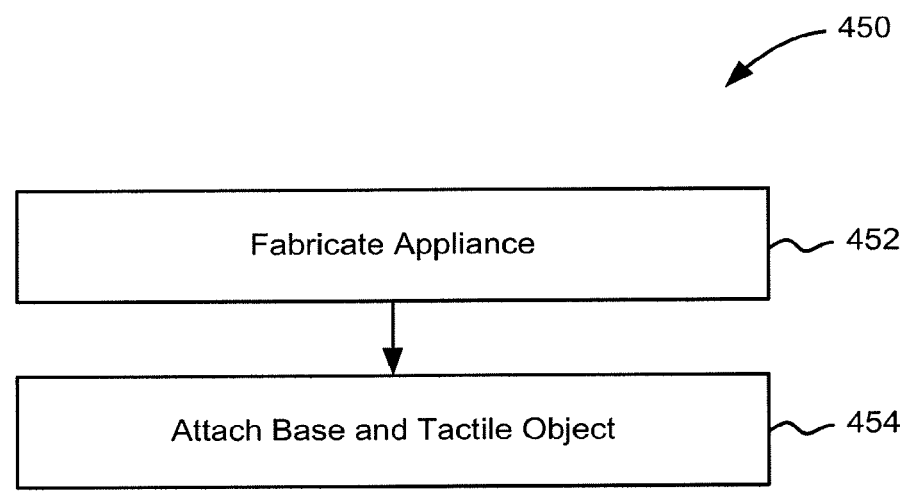
FIG. 10B shows a method for forming a base and a tactile object on an appliance.

FIG. 10B shows a method for forming a base 27 and a tactile object 25 on an appliance 10. In step 452, an appliance 10 is formed. For example, the appliance 10 may be formed in accordance with one of the methods illustrated in FIG. 7A and FIG. 7B and formed to include an inner well within an attachment receiving well 20. In step 454, a base 27 and tactile object 25 are attached to the appliance 10. The base 27 and the tactile object 25 may be a single unit, in which case they are simultaneously bonded to the appliance 10 via adhesives, by elastic forces of the base 27 and/or tactile object 25, and the like. The base 27 and the tactile object 25 may be separate units, in which case they may be separately bonded to the appliance 10 using similar or other suitable methods.

Figure 11:
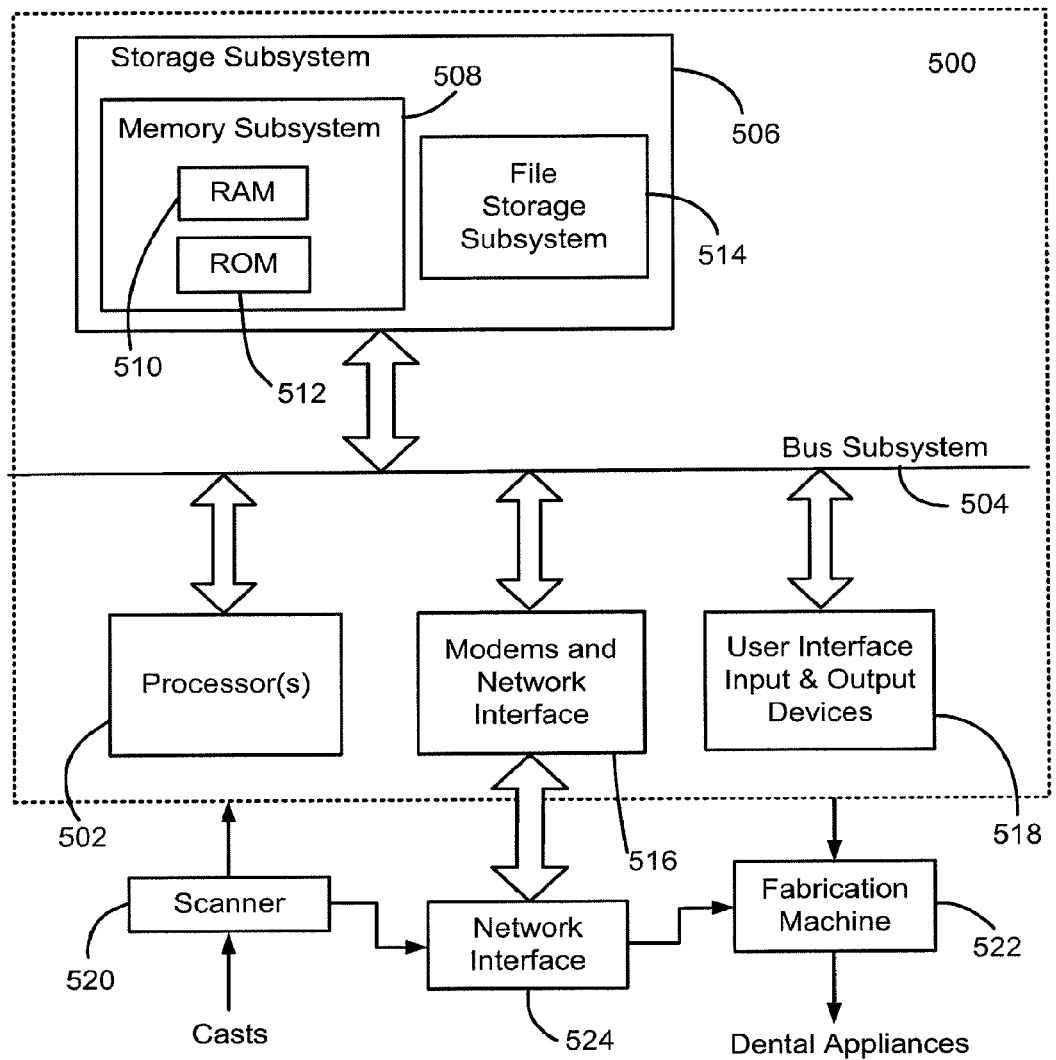
FIG. 11 is a simplified block diagram of a data processing system embodying the present invention.

FIG. 11 is a simplified block diagram of a data processing system 500 embodying the present invention. Data processing system 500 typically includes at least one processor 502 which communicates with a number of peripheral devices via a bus subsystem 504. These peripheral devices typically include a storage subsystem 506 (memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems via a communication network interface 524. Data processing system 500 could be a terminal or a low-end personal computer or a high-end personal computer, workstation, or mainframe.

The user interface input devices typically include a keyboard and may further include a pointing device and a scanner. The pointing device may be an indirect pointing device such as a mouse, trackball, touchpad, or graphics tablet, or a direct pointing device such as a touch screen incorporated into the display. Other types of user interface input devices, such as voice recognition systems, are also possible.

User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 506 maintains the basic programming and data constructs that provide the functionality of the present invention. Software modules used to implement the methods discussed above are typically stored in storage subsystem 506. Storage subsystem 506 typically comprises memory subsystem 508 and file storage subsystem 514.

Memory subsystem 508 typically includes a number of memories including a main random access memory (RAM) 510 for storage of instructions and data during program execution and a read only memory (ROM) 512 in which fixed instructions are stored. In the case of Macintosh-compatible personal computers the ROM would include portions of the operating system; in the case of IBM-compatible personal computers, this would include the BIOS (basic input/output system).

File storage subsystem 514 provides persistent (non-volatile) storage for program and data files, and typically includes at least one hard disk drive and at least one disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that the present invention will most often be implemented in the context of PCs and workstations.

Bus subsystem 504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 520 is responsible for scanning impressions or casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 via network interface 524.

Fabrication machine 522 fabricates orthodontic appliances based on intermediate and final data set information received from data processing system 500. In a distributed environment, fabrication machine 522 may be located at a remote location and receive data set information from data processing system 500 via network interface 524.

One or more structures as described herein may be provided in the form of a kit. For example, a kit may contain one or more of an appliance or plurality (e.g., set) of appliances, tactile object, tooth attachment or components for disposing an attachment on a patients tooth (e.g., attachment material, template, and the like). A receiving cavity of an appliance can be treated or altered, e.g., by chemical means, so as to affect a property of the appliance. A kit can be configured for delivery to an intended recipient (e.g., patient, practitioner, etc.) directly or indirectly. A kit can include an object or component provided separated from an appliance, but which is meant to be coupled with another component. For example, a tactile object can be provided for coupling by a user (e.g., patient, practitioner, etc.) with an appliance.

While the above is a complete description of the preferred embodiments of the invention, various alternatives, modifications, and equivalents may be used. Therefore, the above description should not be taken as limiting the scope of the invention which is defined by the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for orthodontically positioning a patient's tooth, the system comprising:
   an attachment;
   a patient removable orthodontic tooth positioning appliance having teeth receiving cavities shaped to receive and apply a resilient positioning force to the patient's teeth, at least one of the teeth receiving cavities comprising an attachment receiving well having a cross sectional shape that conforms to a cross sectional shape of the attachment and being configured to engage with and receive therein the attachment when the orthodontic appliance is worn by the patient and a force is being applied to the attachment;
   a tactile object disposed between the attachment receiving well and the attachment so as to modulate engagement between the attachment and the attachment receiving well when the orthodontic appliance is worn by the patient; and
   a base disposed in the attachment receiving well, at least part of the tactile object being physically coupled to the base, and at least one of the base and the tactile object being made from a material having an elastic modulus less than an elastic modulus of a material from which the appliance is formed.

2. The system of claim 1, wherein the base is made from a material having an elastic modulus less than the elastic modulus of the appliance material.

3. The system of claim 1, wherein the tactile object is made from a material having an elastic modulus less than the elastic modulus of the appliance material.

4. The system of claim 1, wherein the tactile object is disposed on at least a portion of the attachment.

5. The system of claim 1, wherein the tactile object is disposed on at least a portion of the attachment receiving well.

6. The system of claim 1, wherein the tactile object is located only on the attachment well of the appliance via the base.

7. An orthodontic positioning appliance comprising:
a patient removable orthodontic tooth positioning appliance having teeth receiving cavities shaped to receive and apply a resilient positioning force to the patient's teeth, where at least one of the teeth receiving cavities includes an attachment receiving well shaped to engage with and apply a force to an attachment disposed on the patient's tooth;
a tactile object coupled to the appliance and disposed proximate to the attachment receiving well so as to modulate the engagement between the attachment and the attachment receiving well and the application of force between a surface of the attachment and a surface of the attachment receiving well, when the orthodontic appliance is worn by the patient; and
a base disposed in the attachment receiving well, at least a part of the tactile object being physically coupled to the base, the elastic modulus of the material of the base is less than the elastic modulus of the material of the appliance and the elastic modulus of the material of the tactile object.

8. The orthodontic appliance of claim 7, wherein the material of the tactile object has an elastic modulus less than the material of the appliance.

9. The orthodontic appliance of claim 8, wherein the tactile object comprises a material layer covering one or more surfaces of the attachment receiving well.

10. The orthodontic appliance of claim 8, wherein the tactile object comprises an elongated body extending from a surface of the attachment receiving well via the base.

11. A method for applying a tooth positioning force to the dentition of a patient, the method comprising:
providing an attachment for disposal on at least one of the patient's teeth;
providing a patient removable orthodontic tooth positioning appliance having teeth receiving cavities shaped to receive and apply a resilient positioning force to the patient's teeth, where at least one of the teeth receiving cavities includes an attachment receiving well having a cross sectional shape that conforms to a cross sectional shape of the attachment and being configured to engage with and receive therein the attachment when the orthodontic appliance is worn by the patient and a force is being applied to the attachment;
providing a tactile object for disposal between the attachment receiving well and the attachment so as to modulate force application during engagement between the attachment and the attachment receiving well when the orthodontic appliance is worn by the patient; and
forming a base in the attachment receiving well, wherein at least part of the tactile object is physically coupled to the base, and at least one of the base and the tactile object being made from a material having an elastic modulus less than an elastic modulus of a material from which the appliance is formed.

12. The method of claim 11, wherein the material of the tactile object comprises an elastic modulus less than the elastic modulus of the material from which the appliance is formed and the elastic modulus of the material from which the attachment is formed.

13. The method of claim 11, wherein the tactile object is disposed on at least a portion of the attachment.

14. The method of claim 11, wherein the tactile object is disposed on at least a portion of the attachment receiving well.

15. A method for manufacturing an orthodontic appliance, the method comprising:
generating a patient removable orthodontic tooth positioning appliance having teeth receiving cavities shaped to receive and apply a resilient positioning force to the patient's teeth, where at least one of the teeth receiving cavities includes an attachment receiving well shaped to engage with and apply a force to an attachment disposed on the patient's tooth;
providing a tactile object coupled to the appliance and disposed proximate to the attachment receiving well, for modulating force application during engagement between the attachment and the attachment receiving well and the application of force between a surface of the attachment and a surface of the attachment receiving well, when the orthodontic appliance is worn by the patient; and
disposing a base in the attachment receiving well, wherein at least a part of the tactile object is physically coupled to the base, the elastic modulus of the material of the base is less than the elastic modulus of the material of the appliance and the elastic modulus of the material of the tactile object.

16. The method of claim 15, wherein the material of the tactile object comprises an elastic modulus less than the elastic modulus of the material from which the appliance is formed and the elastic modulus of the material from which the attachment is formed.

17. The method of claim 15, wherein the tactile object is disposed on at least a portion of the attachment.

18. The method of claim 15, wherein the tactile object is disposed on at least a portion of the attachment receiving well.

* * * * *